United States Patent
Moskowitz et al.

(10) Patent No.: US 11,229,525 B2
(45) Date of Patent: *Jan. 25, 2022

(54) BI-DIRECTIONAL FIXATING/LOCKING TRANSVERTEBRAL BODY SCREW/INTERVERTEBRAL CAGE STAND-ALONE CONSTRUCTS HAVING A CENTRAL SCREW LOCKING LEVER, AND PLIERS AND DEVICES FOR SPINAL FUSION

(71) Applicant: Moskowitz Family LLC, Rockville, MD (US)

(72) Inventors: Ahmnon D. Moskowitz, Rockville, MD (US); Nathan C. Moskowitz, Rockville, MD (US); Mosheh T. Moskowitz, Rockville, MD (US); Pablo A. Valdivia Y. Alvarado, Cambridge, MA (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/829,246

(22) Filed: Mar. 25, 2020

(65) Prior Publication Data

US 2020/0345504 A1 Nov. 5, 2020
US 2021/0330469 A9 Oct. 28, 2021

Related U.S. Application Data

(60) Continuation of application No. 16/100,410, filed on Aug. 10, 2018, now Pat. No. 10,603,183, which is a
(Continued)

(51) Int. Cl.
*A61B 17/064* (2006.01)
*A61B 17/068* (2006.01)
(Continued)

(52) U.S. Cl.
CPC ............ *A61F 2/442* (2013.01); *A61B 17/068* (2013.01); *A61B 17/0642* (2013.01);
(Continued)

(58) Field of Classification Search
CPC ........ A61F 2/442; A61F 2/447; A61F 2/4637; A61F 2002/2835; A61F 2002/303331;
(Continued)

(56) References Cited

U.S. PATENT DOCUMENTS 4,554,914 A 11/1985 Kapp et al.
4,599,086 A 7/1986 Doty
(Continued)

FOREIGN PATENT DOCUMENTS

FR 2727003 5/1996
WO WO 2004093749 11/2004
WO WO 2006091503 8/2006

OTHER PUBLICATIONS

Dieter Grob et al., "Clinical Experience With the Dynesys Semirigid Fixation System for the Lumbar Spine," Spine, vol. 30, No. 3, 2005, pp. 324-331.
(Continued)

*Primary Examiner* — Pedro Philogene
(74) *Attorney, Agent, or Firm* — Fish & Richardson P.C.

(57) ABSTRACT

A bi-directional fixating transvertebral (BDFT) screw/cage apparatus including an intervertebral cage for maintaining disc height, and a method of inserting the same is provided. The intervertebral cage includes a first internal screw guide and a second internal screw guide, a first screw member and a second screw member, and a central screw locking lever coupled to the intervertebral cage, wherein the central screw locking lever prevents the first screw member and the second screw from pulling-out of the first internal screw guide and the second internal screw guide. The central screw
(Continued)

locking lever includes a rotatable handle and stem portion, or a screw locking horizontal bracket. A pliers device for inserting and removing the bi-directional fixating transvertebral (BDFT) screw/cage apparatus, a posterior cervical and lumbar facet joint staple, and a staple gun for a posterior cervical and lumbar facet joint staple also are provided.

20 Claims, 40 Drawing Sheets

Related U.S. Application Data continuation of application No. 15/490,107, filed on Apr. 18, 2017, now Pat. No. 10,064,738, which is a continuation of application No. 14/257,650, filed on Apr. 21, 2014, now Pat. No. 9,622,875, which is a division of application No. 12/471,340, filed on May 22, 2009, now Pat. No. 8,734,516, which is a continuation-in-part of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005.

(51) Int. Cl.
   *A61B 17/70* (2006.01)
   *A61B 17/80* (2006.01)
   *A61F 2/44* (2006.01)
   *A61F 2/46* (2006.01)
   A61F 2/30 (2006.01)
   A61B 17/86 (2006.01)
   A61B 17/92 (2006.01)
   A61F 2/28 (2006.01)

(52) U.S. Cl.
   CPC ...... *A61B 17/7064* (2013.01); *A61B 17/7074* (2013.01); *A61B 17/809* (2013.01); *A61F 2/447* (2013.01); *A61F 2/4637* (2013.01); A61B 17/8042 (2013.01); A61B 17/86 (2013.01); A61B 2017/0641 (2013.01); A61B 2017/0647 (2013.01); A61B 2017/0648 (2013.01); A61B 2017/922 (2013.01); A61F 2002/2835 (2013.01); A61F 2002/305 (2013.01); A61F 2002/30331 (2013.01); A61F 2002/30383 (2013.01); A61F 2002/30476 (2013.01); A61F 2002/30517 (2013.01); A61F 2002/30604 (2013.01); A61F 2002/30772 (2013.01); A61F 2002/30787 (2013.01); A61F 2002/30879 (2013.01); A61F 2002/448 (2013.01); A61F 2002/4622 (2013.01); A61F 2002/4641 (2013.01); A61F 2220/0025 (2013.01); A61F 2220/0033 (2013.01); A61F 2220/0041 (2013.01)

(58) Field of Classification Search
   CPC .. A61F 2002/30383; A61F 2002/30476; A61F 2002/305; A61F 2002/30517; A61F 2002/30604; A61F 2002/30772; A61F 2002/30787; A61F 2002/30879; A61F 2002/448; A61F 2002/4622; A61F 2002/4641; A61F 2220/0025; A61F 2220/0033; A61F 2220/0041; A61B 17/0642; A61B 17/068; A61B 17/7064; A61B 17/7074; A61B 17/809; A61B 17/8042; A61B 17/86; A61B 2017/0641; A61B 2017/0647; A61B 2017/0648; A61B 2017/922
   USPC .... 623/17.11–17.16; 606/246–279, 300–328
   See application file for complete search history.

(56) References Cited

U.S. PATENT DOCUMENTS

| | | |
|---|---|---|
| 4,636,217 A | 1/1987 | Ogilvie et al. |
| 4,904,261 A | 2/1990 | Dove et al. |
| 4,960,420 A | 10/1990 | Goble et al. |
| 4,997,432 A | 3/1991 | Keller |
| 5,005,749 A | 4/1991 | Aranyi |
| 5,062,850 A | 11/1991 | Macmillian et al. |
| 5,123,926 A | 6/1992 | Pisharodi |
| 5,290,312 A | 3/1994 | Kojimoto et al. |
| 5,405,391 A | 4/1995 | Henderson et al. |
| 5,413,583 A | 5/1995 | Wohlers |
| 5,454,819 A | 10/1995 | Knoepfler |
| 5,514,180 A | 5/1996 | Heggeness et al. |
| 5,660,188 A | 8/1997 | Groiso |
| 5,667,472 A | 9/1997 | Finn et al. |
| 5,782,832 A | 7/1998 | Larsen et al. |
| 5,865,848 A | 2/1999 | Baker |
| 5,888,223 A | 3/1999 | Bray, Jr. |
| 5,951,574 A | 9/1999 | Stefanchik et al. |
| 5,960,522 A | 10/1999 | Boe |
| 6,126,689 A | 10/2000 | Brett |
| 6,224,602 B1 | 5/2001 | Hayes |
| 6,235,034 B1 | 5/2001 | Bray |
| 6,322,562 B1 | 11/2001 | Wolter |
| 6,342,074 B1 | 1/2002 | Simpson |
| 6,368,350 B1 | 4/2002 | Erickson et al. |
| 6,375,682 B1 | 4/2002 | Fleischmann et al. |
| 6,419,704 B1 | 7/2002 | Ferree |
| 6,432,106 B1 | 8/2002 | Fraser |
| 6,454,807 B1 | 9/2002 | Jackson |
| 6,458,159 B1 | 10/2002 | Thalgott |
| 6,527,804 B1 | 3/2003 | Gauchet et al. |
| 6,533,818 B1 | 3/2003 | Weber et al. |
| 6,558,423 B1 | 5/2003 | Michelson |
| 6,572,653 B1 | 6/2003 | Simonson |
| 6,579,318 B2 | 6/2003 | Varga et al. |
| 6,582,468 B1 | 6/2003 | Gauchet |
| 6,613,055 B2 | 9/2003 | Di Emidio |
| 6,629,998 B1 | 10/2003 | Lin |
| 6,641,614 B1 | 11/2003 | Wagner et al. |
| 6,716,247 B2 | 4/2004 | Michelson |
| 6,719,794 B2 | 4/2004 | Gerber |
| 6,723,126 B1 | 4/2004 | Berry |
| 6,733,532 B1 | 5/2004 | Gauchet et al. |
| 6,764,491 B2 | 7/2004 | Frey et al. |
| 6,770,094 B2 | 8/2004 | Fehling et al. |
| 6,824,564 B2 | 11/2004 | Crozet |
| 6,890,355 B2 | 5/2005 | Michelson |
| 6,904,308 B2 | 6/2005 | Frisch et al. |
| 6,953,477 B2 | 10/2005 | Berry |
| 6,955,671 B2 | 10/2005 | Uchikubo |
| 6,962,606 B2 | 11/2005 | Michelson |
| 6,972,019 B2 | 12/2005 | Michelson |
| 7,030,904 B2 | 4/2006 | Adair et al. |
| 7,033,394 B2 | 4/2006 | Michelson |
| 7,037,258 B2 | 5/2006 | Chatenever et al. |
| 7,097,615 B2 | 8/2006 | Banik et al. |
| 7,135,043 B2 | 11/2006 | Akahara et al. |
| 7,211,112 B2 | 5/2007 | Baynham et al. |
| 7,232,464 B2 | 6/2007 | Mathieu et al. |
| 7,238,203 B2 | 7/2007 | Bagga et al. |
| 7,326,248 B2 | 2/2008 | Michelson |
| 7,442,209 B2 | 10/2008 | Michelson |
| 7,615,059 B2 | 11/2009 | Watschke et al. |

(56) References Cited

U.S. PATENT DOCUMENTS

| | | | |
|---|---|---|---|
| 7,776,047 B2 | 8/2010 | Fanger et al. | |
| 7,862,616 B2 | 1/2011 | Lechmann et al. | |
| 7,985,255 B2 | 7/2011 | Bray et al. | |
| 8,034,060 B2 | 10/2011 | Keren et al. | |
| 8,268,000 B2 | 9/2012 | Waugh et al. | |
| 8,328,872 B2 | 12/2012 | Duffield et al. | |
| 8,403,986 B2 | 3/2013 | Michelson | |
| 8,425,607 B2* | 4/2013 | Waugh | A61F 2/447 623/17.16 |
| 8,734,516 B2* | 5/2014 | Moskowitz | A61F 2/442 623/17.11 |
| 8,790,405 B2 | 7/2014 | Biedermann et al. | |
| 9,622,875 B2 | 4/2017 | Moskowitz | |
| 9,889,022 B2 | 2/2018 | Moskowitz | |
| 9,895,238 B2 | 2/2018 | Moskowitz | |
| 10,064,738 B2* | 9/2018 | Moskowitz | A61F 2/447 |
| 10,603,183 B2* | 3/2020 | Moskowitz | A61B 17/7064 |
| 2002/0068977 A1 | 6/2002 | Jackson | |
| 2002/0143338 A1 | 10/2002 | Orbay et al. | |
| 2004/0088054 A1 | 5/2004 | Berry | |
| 2004/0177531 A1 | 9/2004 | DiBenedetto et al. | |
| 2004/0186569 A1 | 9/2004 | Berry | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0177235 A1 | 8/2005 | Baynham et al. | |
| 2005/0216084 A1 | 9/2005 | Fleischmann | |
| 2005/0256576 A1 | 11/2005 | Moskowitz et al. | |
| 2005/0261769 A1 | 11/2005 | Moskowitz et al. | |
| 2005/0273170 A1 | 12/2005 | Navarro et al. | |
| 2005/0278026 A1 | 12/2005 | Gordon et al. | |
| 2006/0241621 A1 | 10/2006 | Moskowitz et al. | |
| 2007/0049943 A1 | 3/2007 | Moskowitz et al. | |
| 2007/0167678 A1 | 7/2007 | Moskowitz et al. | |
| 2007/0198089 A1 | 8/2007 | Moskowitz et al. | |
| 2007/0213820 A1 | 9/2007 | Magerl et al. | |
| 2007/0250172 A1 | 10/2007 | Moskowitz et al. | |
| 2008/0033440 A1 | 2/2008 | Moskowitz et al. | |
| 2008/0177307 A1 | 7/2008 | Moskowitz et al. | |
| 2008/0281424 A1 | 11/2008 | Parry et al. | |
| 2009/0105831 A1* | 4/2009 | Jones | A61B 17/8042 623/17.16 |
| 2009/0112271 A1 | 4/2009 | Moskowitz et al. | |
| 2009/0224023 A1 | 9/2009 | Moskowitz et al. | |
| 2009/0234455 A1 | 9/2009 | Moskowitz et al. | |
| 2010/0145460 A1* | 6/2010 | McDonough | A61B 17/7059 623/17.16 |
| 2010/0324606 A1 | 12/2010 | Moskowitz et al. | |
| 2011/0125269 A1 | 5/2011 | Moskowitz et al. | |
| 2011/0137349 A1 | 6/2011 | Moskowitz et al. | |
| 2011/0178600 A1 | 7/2011 | Moskowitz et al. | |
| 2011/0208312 A1 | 8/2011 | Moskowitz et al. | |
| 2011/0288646 A1 | 11/2011 | Moskowitz et al. | |
| 2011/0295327 A1 | 12/2011 | Moskowitz et al. | |
| 2011/0295371 A1 | 12/2011 | Moskowitz et al. | |
| 2011/0307011 A1 | 12/2011 | Moskowitz et al. | |
| 2011/0319935 A1 | 12/2011 | Moskowitz et al. | |
| 2012/0010714 A1 | 1/2012 | Moskowitz et al. | |
| 2012/0330419 A1 | 12/2012 | Moskowitz et al. | |
| 2013/0018468 A1 | 1/2013 | Moskowitz et al. | |
| 2013/0018469 A1 | 1/2013 | Moskowitz et al. | |
| 2013/0018470 A1 | 1/2013 | Moskowitz et al. | |
| 2013/0023991 A1 | 1/2013 | Moskowitz et al. | |
| 2013/0023992 A1 | 1/2013 | Moskowitz et al. | |
| 2013/0053962 A1 | 2/2013 | Moskowitz et al. | |
| 2013/0173002 A1 | 7/2013 | Moskowitz et al. | |
| 2013/0282017 A1 | 10/2013 | Moskowitz et al. | |
| 2014/0249629 A1 | 9/2014 | Moskowitz et al. | |
| 2015/0025637 A1 | 1/2015 | Moskowitz et al. | |
| 2015/0105824 A1 | 4/2015 | Moskowitz et al. | |
| 2015/0148847 A1 | 5/2015 | Moskowitz et al. | |
| 2016/0374830 A1 | 12/2016 | Moskowitz et al. | |
| 2017/0252178 A1 | 9/2017 | Moskowitz et al. | |
| 2018/0036134 A1 | 2/2018 | Moskowitz et al. | |

OTHER PUBLICATIONS

E.K. Wai et al., "Disk Replacement Arthroplasties: Can The Success of Hip and Knee Replacements be Repeated in the Spine?," Seminars in Spine Surgery, vol. 15, No. 4 Dec. 2003, pp. 473-482.

International Search Report (ISR) and Written Opinion of the International Searching Authority, dated Dec. 3, 2007, International Application No. PCT/US 07/05005.

International Search Report (ISR) and Written Opinion of the International Searching Authority, dated May 21, 2008. International Application No. PCT/US2007/021015.

International Search Report (ISR) and Written Opinion of the International Searching Authority, dated Jul. 9, 2008. International Application No. PCT/US2007/021013.

Richard D. Guyer et al., "Intervertebral Disc Prostheses," Spine Journal, vol. 28, No. 15S, Supp. To Aug. 1, 2003, pp. S15-S23.

Vincent C. Traynelis, "Prosthetics and Biologies: The Wave of the Future," Clinical Neurosurgery, vol. 50, Proceedings of the Congress of Neurological Surgeons, Philadelphia, PA 2002, Chapter 9, pp. 207-219.

* cited by examiner

BI-DIRECTIONAL FIXATING/LOCKING TRANSVERTEBRAL BODY SCREW/INTERVERTEBRAL CAGE STAND-ALONE CONSTRUCTS HAVING A CENTRAL SCREW LOCKING LEVER, AND PLIERS AND DEVICES FOR SPINAL FUSION

This application is a Continuation of Ser. No. 16/100,410, filed Aug. 10, 2018, which is a Continuation of Ser. No. 15/490,107 filed Apr. 18, 2017, now U.S. Pat. No. 10,064,738 issued Sep. 4, 2018, which is a Continuation of Ser. No. 14/257,650 filed Apr. 21, 2014, now U.S. Pat. No. 9,622,975 issued Apr. 18, 2017, which is a Divisional Application of Ser. No. 12/471,340 filed May 22, 2009, now U.S. Pat. No. 8,734,516 issued May 27, 2014, which is a Continuation-In-Part Application of application Ser. No. 12/054,335 filed on Mar. 24, 2008, now U.S. Pat. No. 7,972,363 issued Jul. 5, 2011, which is a Continuation-In-Part of application Ser. No. 11/842,855, filed on Aug. 21, 2007, now U.S. Pat. No. 7,942,903 issued May 17, 2011, which is a Continuation-In-Part of application Ser. No. 11/536,815, filed on Sep. 29, 2006, now U.S. Pat. No. 7,846,188 issued Dec. 7, 2010, which is a Continuation-In-Part of application Ser. No. 11/208,644, filed on Aug. 23, 2005, now U.S. Pat. No. 7,704,279 issued Apr. 27, 2010, and this application also claims priority under 35 U.S.C. § 119(e) of U.S. Provisional Application No. 60/670,231, filed on Apr. 12, 2005; the entire contents of all of the above identified patent applications are hereby incorporated by reference in their entirety.

This application is related to applicants' U.S. Pat. No. 8,257,370 issued Sep. 4, 2012, titled "POSTERIOR CERVICAL AND LUMBAR INTERARTICULATING JOINT STAPLES, STAPLING GUNS, AND DEVICES FOR SPINAL FUSION", which is incorporated herein by reference.

FIELD OF DISCLOSURE

The present invention relates to a unique universal bi-directional screw (BDS) system, and in particular its application to the spine, also referred to as bi-directional fixating transvertebral (BDFT) screw/cage constructs which can be used as stand-alone intervertebral devices which combine the dual functions of an intervertebral spacer that can be filled with bone fusion material(s), as well as a bi-directional transvertebral bone fixating/fusion screw apparatus. In the posterior lumbosacral and thoracic spine, intervertebral cage/BDFT screw constructs can be used as stand-alone devices obviating the need for pedicle screw fixation in many but not all cases. In the anterior cervical, thoracic and lumbosacral spine, intervertebral cage/BDFT screw constructs can be used as stand-alone devices obviating the need for anterior or lateral (thoracic) spinal plating, and/or supplemental posterior pedicle screw fixation.

The present invention also relates to percutaneous stand-alone or supplemental posterior cervical, thoracic and lumbosacral calibrated intrerarticulating joint staple guns and staples which may obviate and/or lessen the need for posterior supplemental pedicle screw fixation.

BACKGROUND

The history and evolution of instrumented spinal fusion in the entire human spine has been reviewed in related application Ser. No. 12/054,335 filed on Mar. 24, 2008, Ser. No. 11/842,855, filed on Aug. 21, 2007, Ser. No. 11/536,815 filed on Sep. 29, 2006, and Ser. No. 11/208,644 filed on Aug. 23, 2005, the contents of which are hereby incorporated by reference in their entirety. Conventionally, the majority of posterior cervical and almost all posterior thoracic and lumbosacral fusion surgical techniques are typically supplemented with pedicle screw placement. Conventionally, the majority of anterior cervical spinal fusions, and many anterio-lateral thoracic, and anterior or anterio-lateral lumbosacral fusions are supplemented with anterior or anterior-lateral spinal plating, and very often, in particular in the thoracic and lumbosacral spine, are supplemented with posterior pedicle screw instrumentation.

Complications of pedicle screw placement in cervical, thoracic and lumbosacral spine include duration of procedure, significant tissue dissection and muscle retraction, misplaced screws with neural and/or vascular injury, excessive blood loss, need for transfusions, prolonged recovery, incomplete return to work, and excessive rigidity leading to adjacent segmental disease requiring further fusions and re-operations. Recent advances in pedicle screw fixation including minimally invasive, and stereotactic CT image-guided technology, and the development of flexible rods, imperfectly address some but not all of these issues.

Complications of anterior plating in the cervical spine include potential plate, and/or screw esophageal compression, and misplaced screws leading to neurovascular injury. Complications of anterior plating in the anterior lumbar spine include potential devastating injury to the major vessels due to chronic vascular erosion of the major vessels, or acute vascular injuries due to partial or complete plate and/or screw back out. Furthermore, for re-do surgeries, plate removal can be arduous, with potential complications of prolonged esophageal retraction, vascular injury and screw breakage. Recent advances including diminishing the plate width and/or profile, and absorbable plates, imperfectly address some but not all of these issues.

Complications of all conventional spinal anterior intervertebral device constructs are their potential for extrusion in the absence of plating. Hence, they are supplemented with anterior plating to prevent extrusion. Complications of posterior lumbosacral intervertebral device construct in the presence or absence of supplemental pedicle screw fixation is device extrusion, and potential nerve root injuries related to retraction.

SUMMARY

Herein described are multiple device embodiments which combine in a single stand-alone construct the dual functions of: a) an intervertebral cage spacer which can be filled with bone fusion material maintaining disc height, and, b) a bi-directional fixating/fusion transvertebral body screw apparatus. These embodiments are described for posterior and anterior lumbar (and anterio-lateral thoracic) intervertebral placement, and anterior cervical intervertebral placement. The present invention recognizes the aforementioned problems with conventional apparatus and solves these problems by, among other things, improving upon the designs illustrated in the aforementioned related applications. The present application provides an advanced and novel bi-directional fixating transvertebral (BDFT) screw/cage apparatus having, for example, more advanced screw locking embodiments that prevent screw pull-out or back-out.

The exemplary embodiments of a bi-directional fixating transvertebral (BDFT) screw/cage apparatus provide as strong or stronger segmental fusion as pedicle screws without the complications arising from pedicle screw placement, which include misplacement with potential nerve and/or vascular injury, violation of healthy facets, possible pedicle destruction, blood loss, and overly rigid fusions. By placing screws across the intervertebral space from vertebral body to vertebral body, engaging anterior and middle spinal columns and not the vertebral bodies via the transpedicular route thereby excluding the posterior spinal column, then healthy facet joints, if they exist, are preserved. Because the present invention accomplishes both anterior and middle column fusion, without rigidly fixating the posterior column, the present invention in essence creates a flexible fusion.

The present invention recognizes that the very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss and significant reduction in O.R. time. Thus, the complication of pedicle screw pull out, and hence high re-operation rate associated with the current embodiment of flexible fusion pedicle screws/rods is obviated. The lumbosacral intervertebral cage/BDFT screw constructs can be introduced via posterior lateral, transforaminal or anterior interbody fusion approaches/surgical techniques. Although one can opt to supplement these constructs with transpedicular screws there would be no absolute need for supplemental pedicle screw fixation with these operative techniques.

The anterior placement of a bi-directional fixating transvertebral (BDFT) screw/cage apparatus according to the embodiments of the present invention into the cervical and lumbar spine obviates the need for supplemental anterior cervical or anterior lumbar plating. The sole purpose of these plates is to prevent intervertebral device extrusion. This function is completely obviated and replaced by the dual functioning bi-directional fixating transvertebral (BDFT) screw/cage apparatus, according to the present invention. The obvious advantage of this is a significant savings in operative time, and prevention of injuries associated with plating, in particular esophageal, large and small vessel injuries, and spinal cord nerve root injuries.

Because the embodiments of the bi-directional fixating transvertebral (BDFT) screw/cage apparatus engage a small percentage of the rostral and caudal vertebral body surface area, multi-level fusions can be performed with these devices.

The aforementioned related applications described a novel calibrated lumbar/thoracic stapling device which staples the inferior articulating facet of the superior spinal segment to the superior articulating facet of the inferior vertebral segment unilaterally or bilaterally, which may minimize motion until interbody fusion occurs. The present invention presents an evolved and lumbar staple gun which is far more user friendly than previously described embodiments by incorporating a new release mechanism, as described in the aforementioned related applications. This new change simplifies the earlier design, and facilitates easier insertion and removal of the staple decreasing the risk of the staple becoming loose or falling off during an operation. The exemplary staple gun thus makes posterior lumbar facet stapling far more amenable for percutaneous fluoroscopically guided surgical stapling.

The aforementioned related applications introduced a novel posterior cervical facet stapling device which staples the inferior articulating facet of the superior cervical segment with the superior articulating facet of the inferior cervical segment either unilaterally or bilaterally. The advantage of cervical facet staples is speed and safety. The risks of cervical facet pedicle screw fixation, which include nerve root and vertebral artery injuries, are completely obviated by the use of the embodiments of the present invention. Thus, cervical facet staples achieve the same function of cervical pedicle screws without the risks.

Placement of different embodiments of the cervical facet staples which include those with two or four prongs, along unilateral and/or bilateral facet joints in a modular manner, lead to different degrees of calibrated joint motion hence introducing the novel concept of calibrated cervical fusion. In the related applications, cervical facet embodiments of a highly evolved cervical staple gun for the two and four pronged cervical staples were introduced. The staple gun included a built-in trigger, trigger spring, spring hook, and return spring polyethylene cushion that improved the strength, ease and speed of staple bone penetration. In this application, the embodiments can provide more simplified and economically efficient staple guns which are very user friendly and further enhances the application of the cervical staple gun also making posterior cervical facet stapling more amenable to a non-invasive, percutaneous surgical procedure.

Conventionally, failed anterior lumbar arthroplasties are salvaged by combined anterior and posterior fusions. Intervertebral cage/BDFT screw constructs may be utilized as a one-step salvage mechanism for failed/extruded anteriorly placed lumbar artificial discs obviating the need for supplemental posterior pedicle screws and/or anterior lumbar plating thereby significantly reducing and/or eliminating co-morbidities associated with these other salvage procedures.

Likewise, anterior cervical intervertebral cage/BDFT screw construct placement can be used to salvage failed anterior cervical arthroplasties, and re-do fusions without having to supplement with cervical anterior plates, thereby reducing the morbidity of this procedure.

In addition, if a patient develops a discogenic problem necessitating anterior cervical discectomy and fusion at a level above or below a previously fused and plated segment, the present invention reduces or eliminates the need to remove the prior plate in order to place a new superior plate, because the function of the plate is replaced by the dual functioning intervertebral cervical construct, thereby reducing the operating room time and surgical morbidity of this procedure.

Furthermore, because of the orientation and length of the BDFT screws within the intervertebral cage/BDFT constructs, multiple level fusions can be easily performed. Posterior cervical and lumbar stapling can also be performed for multiple levels.

For example, an exemplary embodiment is directed to an intervertebral cage spacer and bi-directional fixating/fusion transvertebral body screw/cage apparatus, a posterior lumbar facet staple and a staple gun for a posterior lumbar facet staple, and a staple gun for a posterior cervical facet joint staple are provided. The apparatus includes an intervertebral cage for maintaining disc height. The intervertebral cage includes a first internal screw guide and a second internal screw guide. The apparatus further includes a first screw member having a tapered end and a threaded body disposed within the intervertebral cage, a second screw member having a tapered end and a threaded body disposed within the intervertebral cage, The device includes a novel mechanism involving a separate screw locking bracket with hooks that insert into a prefabricated insertion site within the sides of the intervertebral cage which when press-fit onto the cage prevents the screw members from pulling-out of the internal screw guides. A specifically designed set of pliers is illustrated which can be used to insert the locking brackets. The tips have stops so that the brackets can be more easily held. It also has a limiting screw to limit the amount the pliers close to prevent over-pressing the locking brackets. It also has a leaf spring that preloads the pliers. These appliers can also apply gentle pressure on the brackets flexure grips (side tabs) to slightly deform (open) the bracket hooks, thus easily removing the bracket if necessary intra-operatively or in the future.

Another exemplary embodiment is directed to a staple gun for a posterior lumbar facet joint staple gun, including a handle having a first grip and a second grip, a cylinder body having a first end for receiving the posterior lumbar facet joint staple and a second end adjacent to the handle, a connector that connects the cylinder body to the handle, a puller, an independent puller tip and a return spring. This embodiment is more user friendly making the staple gun easier to load, easier to use, and prevents the staple from falling off during any portion of the surgery.

Yet another exemplary embodiment is directed to a staple gun for a posterior cervical facet joint staple, including a handle, a retaining spring, a central plunger and a tip. The device can be used with a hammer to apply two or four pronged posterior cervical staples to impact them into the facets. A central button releases the staple from the spring allowing the staple gun to be reloaded.

Another exemplary embodiment is directed to a method of inserting a bi-directional fixating transvertebral (BDFT) screw/cage apparatus between a first vertebral body and a second vertebral body. The method includes measuring a dimension of a disc space between the first vertebral body and the second vertebral body, determining that the disc space is a posterior lumbar disc space, an anterior lumbar disc space, or an anterior cervical disc space, selecting an intervertebral cage based on the measured dimension of the disc space and based on the determination of the disc space being the posterior lumbar disc space, the anterior lumbar disc space, or the anterior cervical disc space, inserting the selected intervertebral cage into a midline of the disc space until the selected intervertebral cage is flush or countersunk relative to the first vertebral body and the second vertebral body, inserting a first screw member into a first internal screw guide of the selected intervertebral cage, inserting a second screw member into a second internal screw guide of the selected intervertebral cage, screwing the first screw member and the second screw member into the first vertebral body and the second vertebral body respectively, confirming a position and placement of the intervertebral cage relative to the first vertebral body and the second vertebral body, and locking the first screw member and the second screw member in a final position by embedding a portion of the first screw member and the second screw member into a screw locking mechanism of the selected intervertebral cage.

Once the surgeon is satisfied with the position and placement of the cage, the screws can then be locked in their final positions. Then a screw locking bracket is applied with the special plier tool on top of the cage allowing the bracket hooks to snap into the cage inserts. If the surgeon changes his mind intra-operatively, or if in a future date the construct needs to be removed, the surgeon presses on the side tabs with a pliers embodiment to slightly deform (open) the bracket hooks and can then easily remove the locking bracket. Multiple level placements can be performed including two, three or more levels if necessary.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION

Figure 1A:
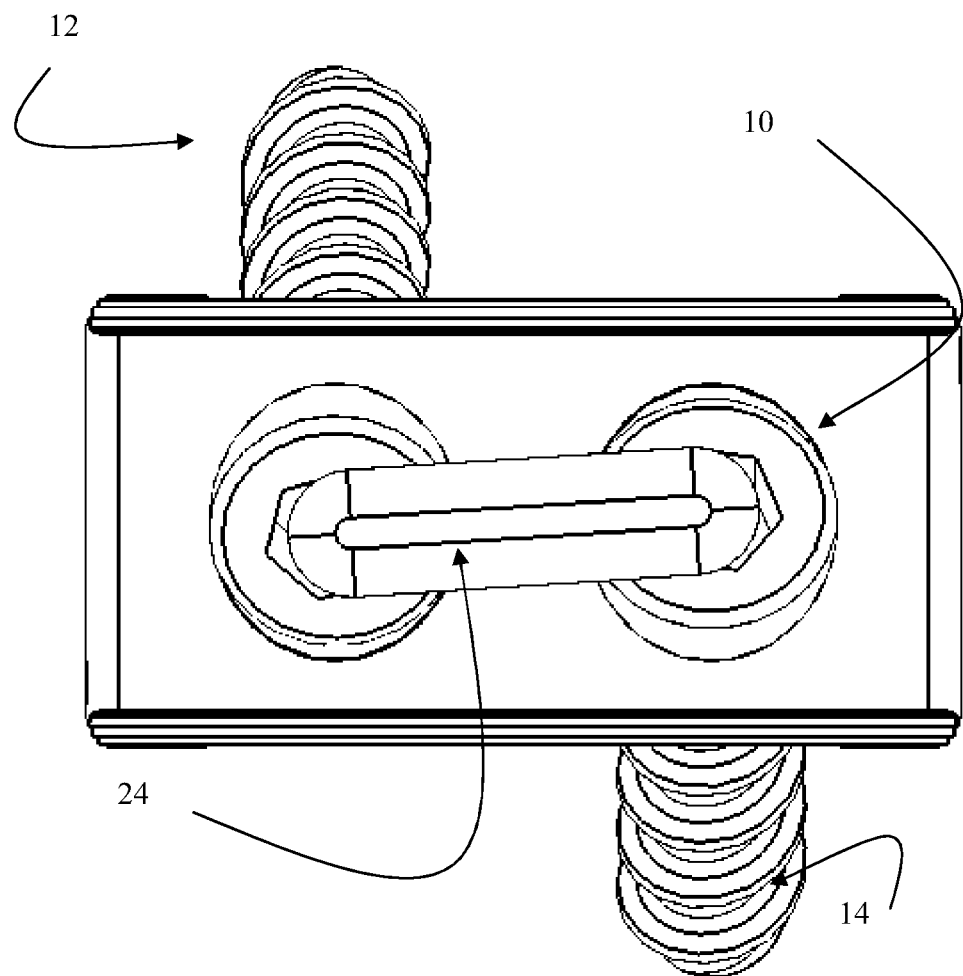
FIGS. 1A-E illustrate an embodiment of an anterior cervical intervertebral cage/BDFT screw construct with a central screw locking lever in top (FIG. 1A), bottom isometric (FIG. 1B), side (FIG. 1C), isometric front (FIG. 1D), isometric bottom, and isometric fully exploded with visualized internalized angled screw guides (FIG. 1E) views.
Figure 1B:
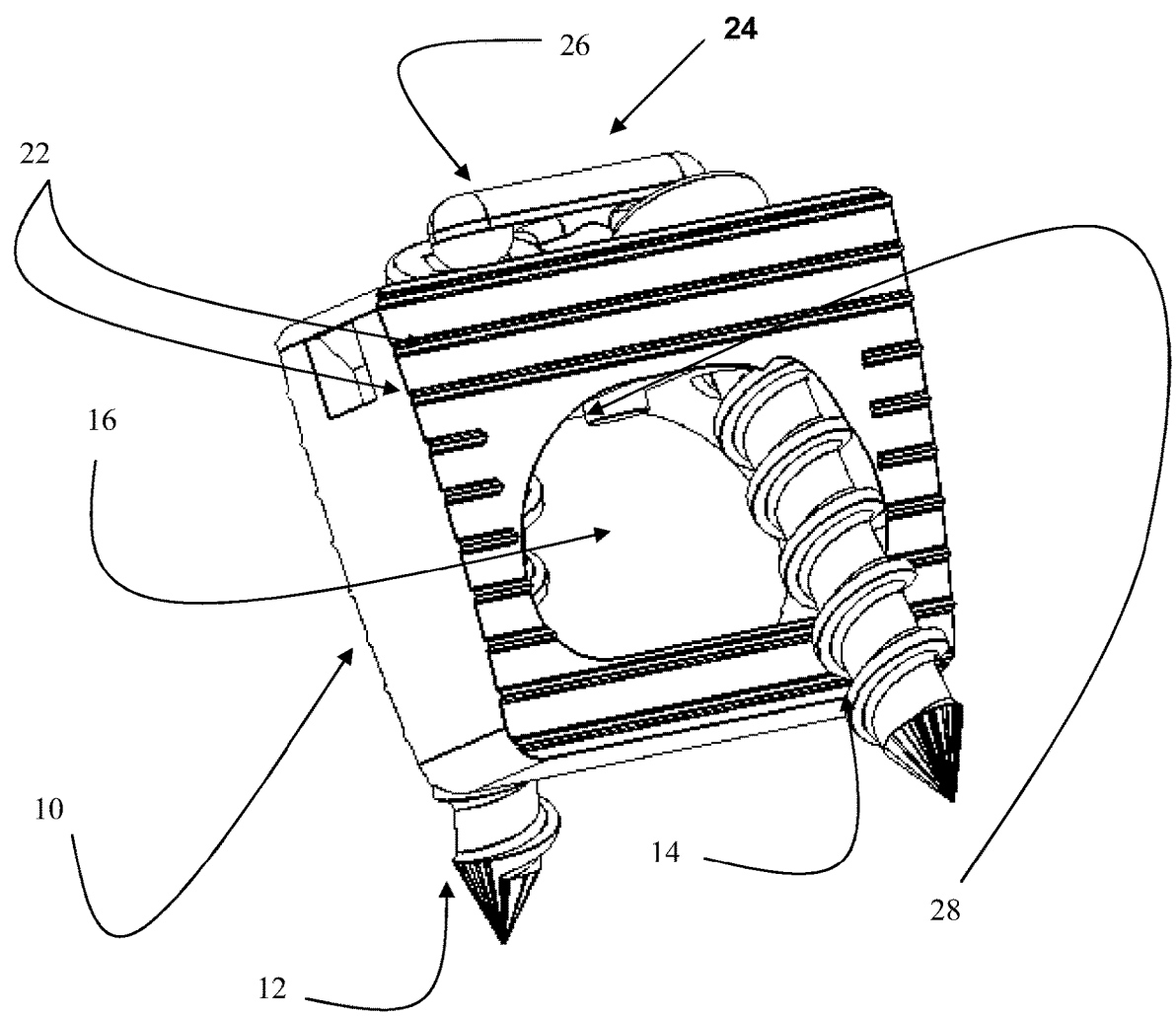
Figure 1C:
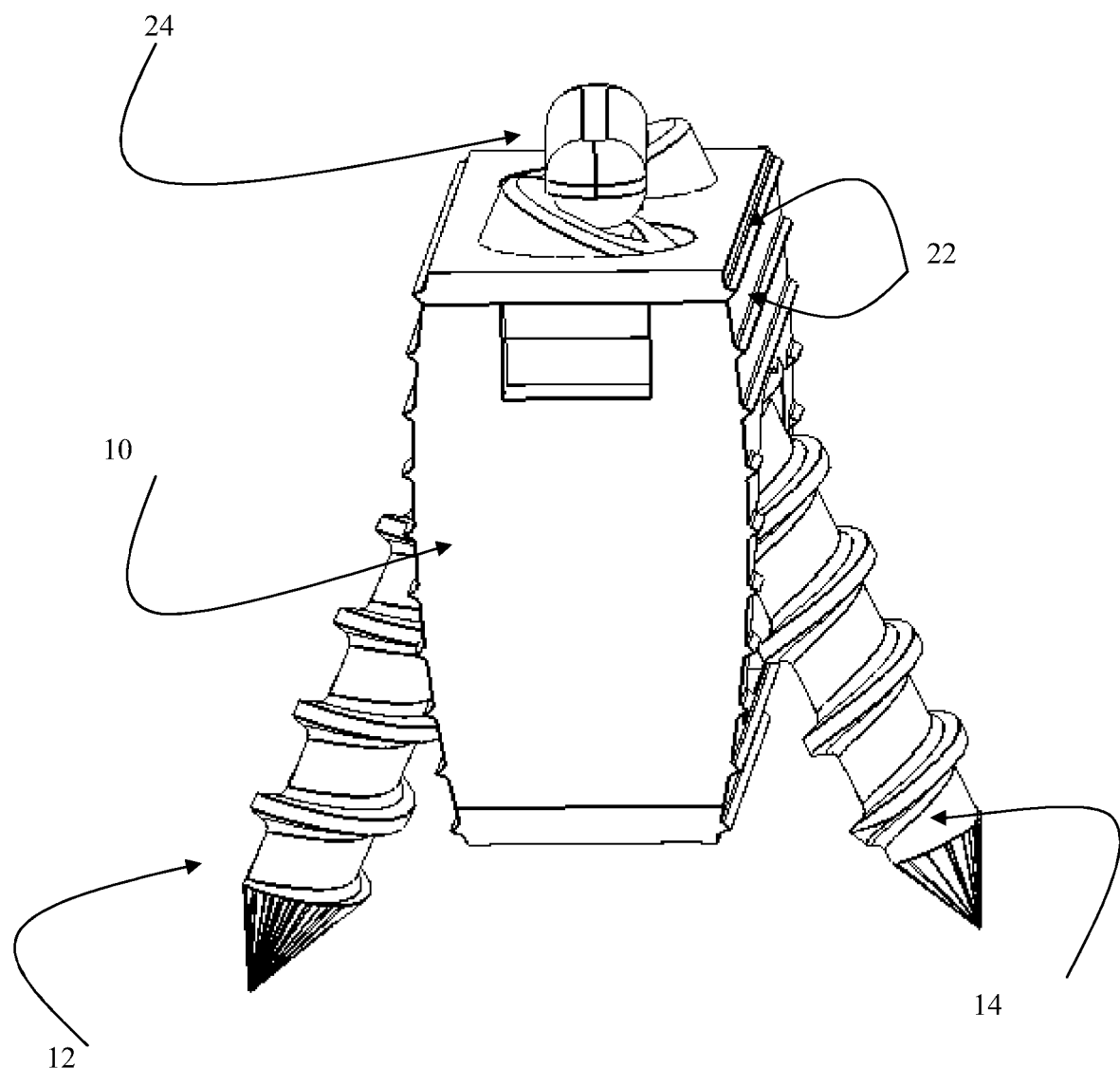
Figure 1D:
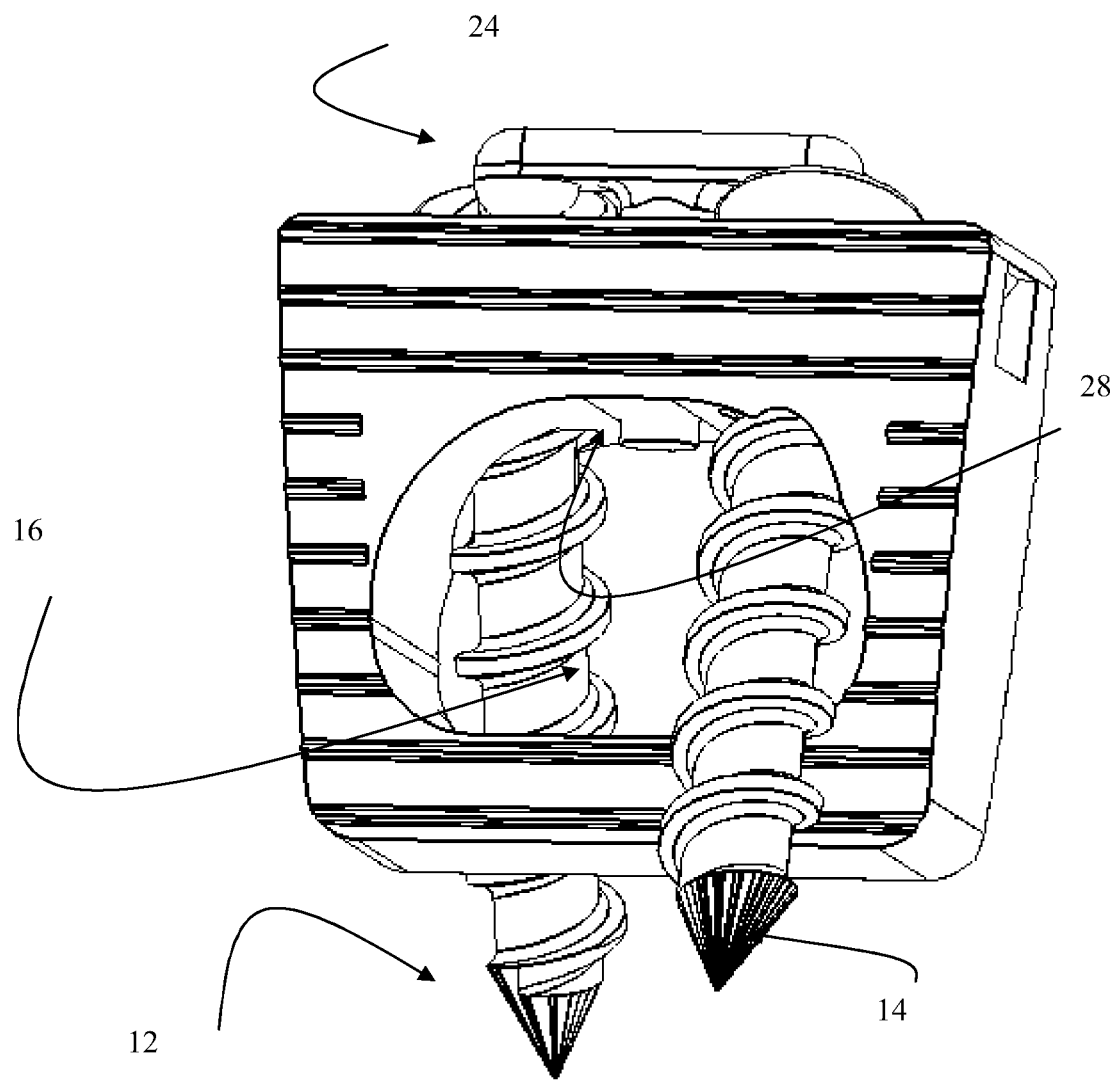

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

With reference to FIGS. 1A-10C, exemplary embodiments of the invention will now be described.

1. The Medical Device

Referring to FIGS. 1-5, the above described problems of the conventional art can be solved in the cervical, thoracic and lumbosacral spines by insertion into the denuded intervertebral disc space multiple embodiments of a bi-directional fixating transvertebral (BDFT) screw/cage apparatus.

For example, FIGS. 1A-E illustrate three-dimensional views of an embodiment of an anterior cervical intervertebral cage/BDFT construct 10. In this embodiment, the cage is elliptically contoured (FIG. 1C; side view) to fit into the bi-concave cervical disc space. The embodiment includes two screws 12, 14. A first screw 12 is oriented rostrally (superiorly) and a second screw 14 is oriented caudally (inferiorly). The cage 10 can include a cavity 16 for bone product placement. The cage 10 includes two built in internalized screw/drill guides 18, 20, one for each screw 12, 14 which orient the screws bi-directionally in opposite directions. One of ordinary skill in the art will recognize that the internalized screw/drill guides 18, 20 can have different degrees of angulation and/or different positions within the cage 10. The built in tunnels of the screw guides 18, 20 provide an important advantage of ensuring that only one prescribed angled trajectory is possible for transvertebral screw placement. Embodiments of the intervertebral cages 10 can be designed with internalized screw/drill guides 18, 20 with different angles and/or different positions within the cage 10. The angle and size of the screws 12, 14 make them amenable to single or multi-level placement. The superior and inferior surfaces or edges of the lumbar cage 10 can include ridges 22 to facilitate integration and fusion with superior and inferior vertebral bodies.

Figure 1E:
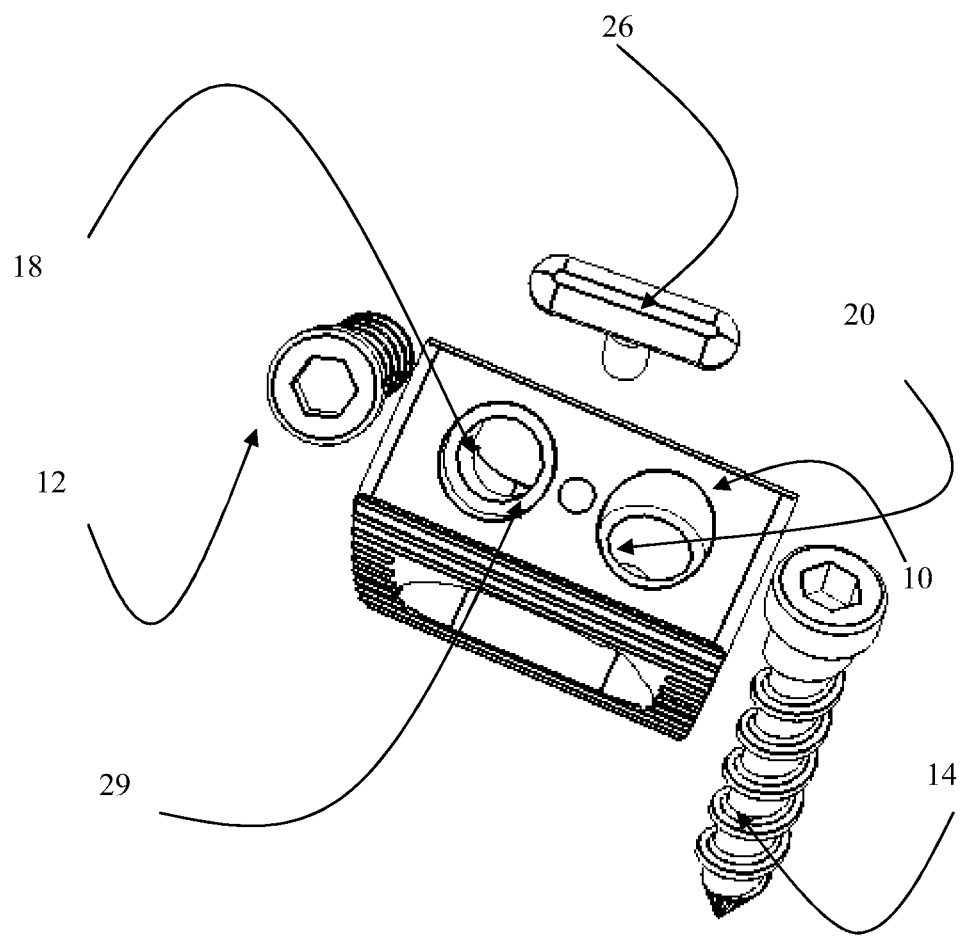
Figure 2A:
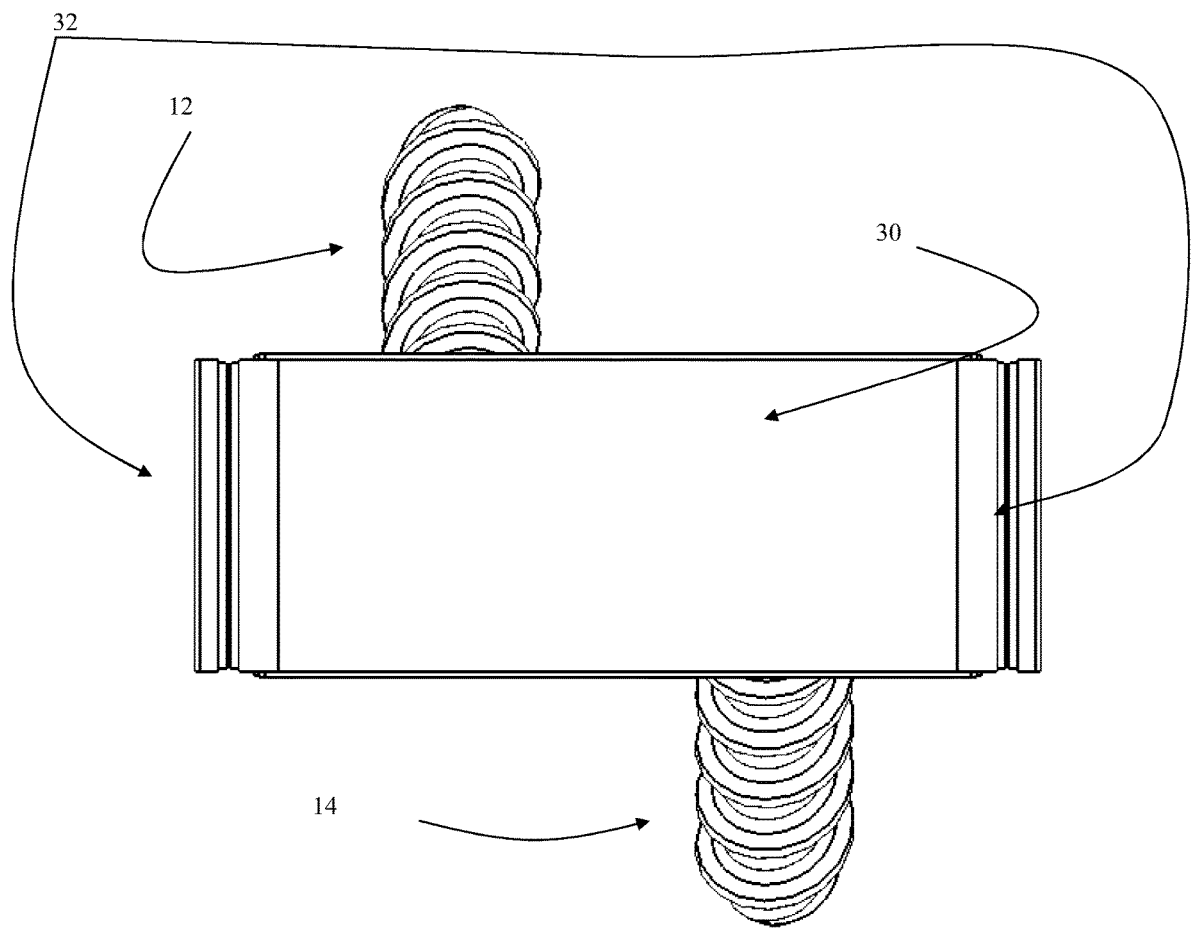
FIGS. 2A-E illustrate an embodiment of an intervertebral cage/BDFT screw construct with screw locking bracket in top (FIG. 2A), bottom isometric (FIG. 2B), side isometric (FIG. 2C), top isometric fully explodes with visualized internal screw guides (FIG. 2D), and bottom isometric fully exploded with visualized bracket hooks and flexion grips (FIG. 2E) views.
Figure 2B:
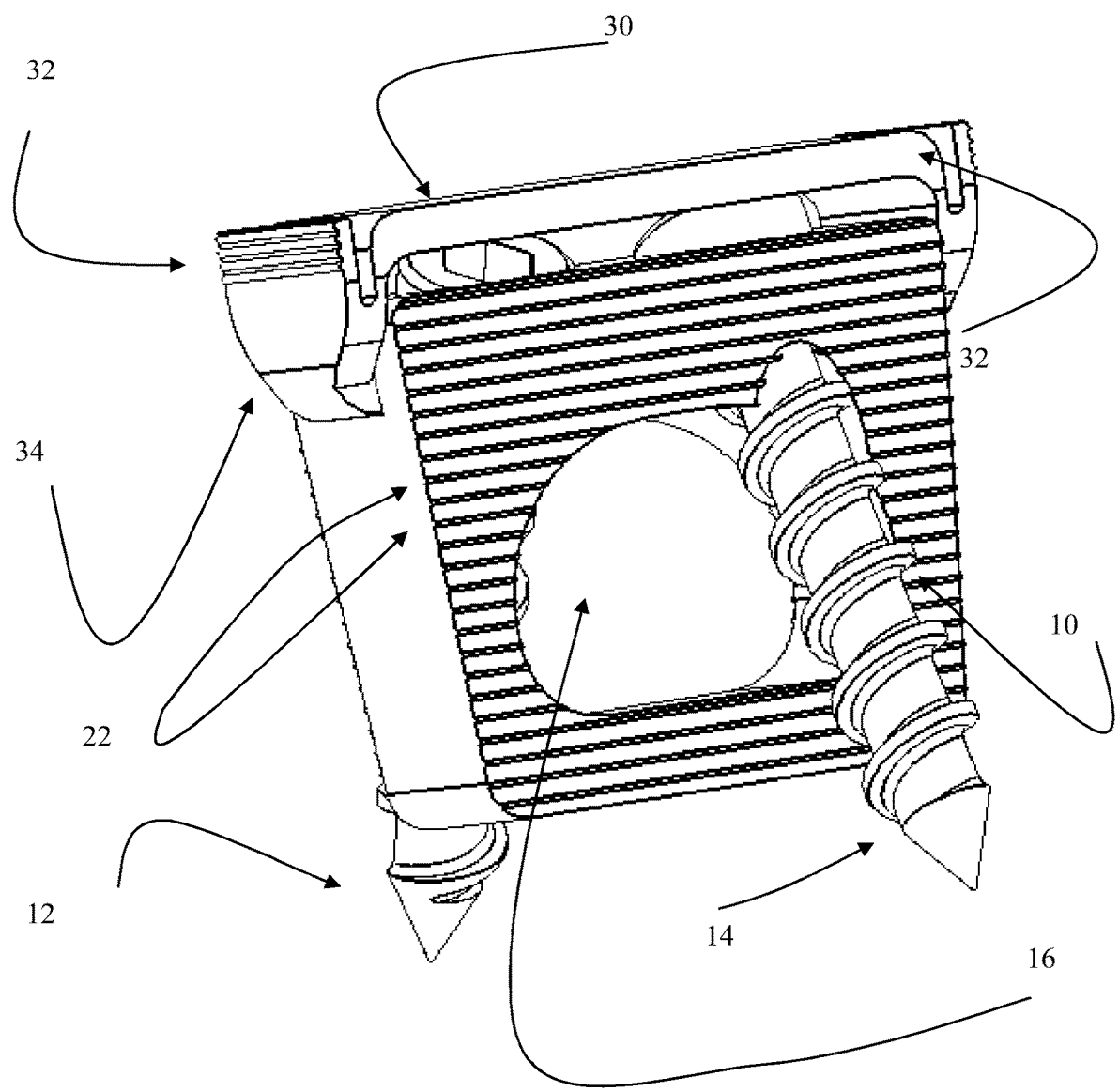
Figure 2C:
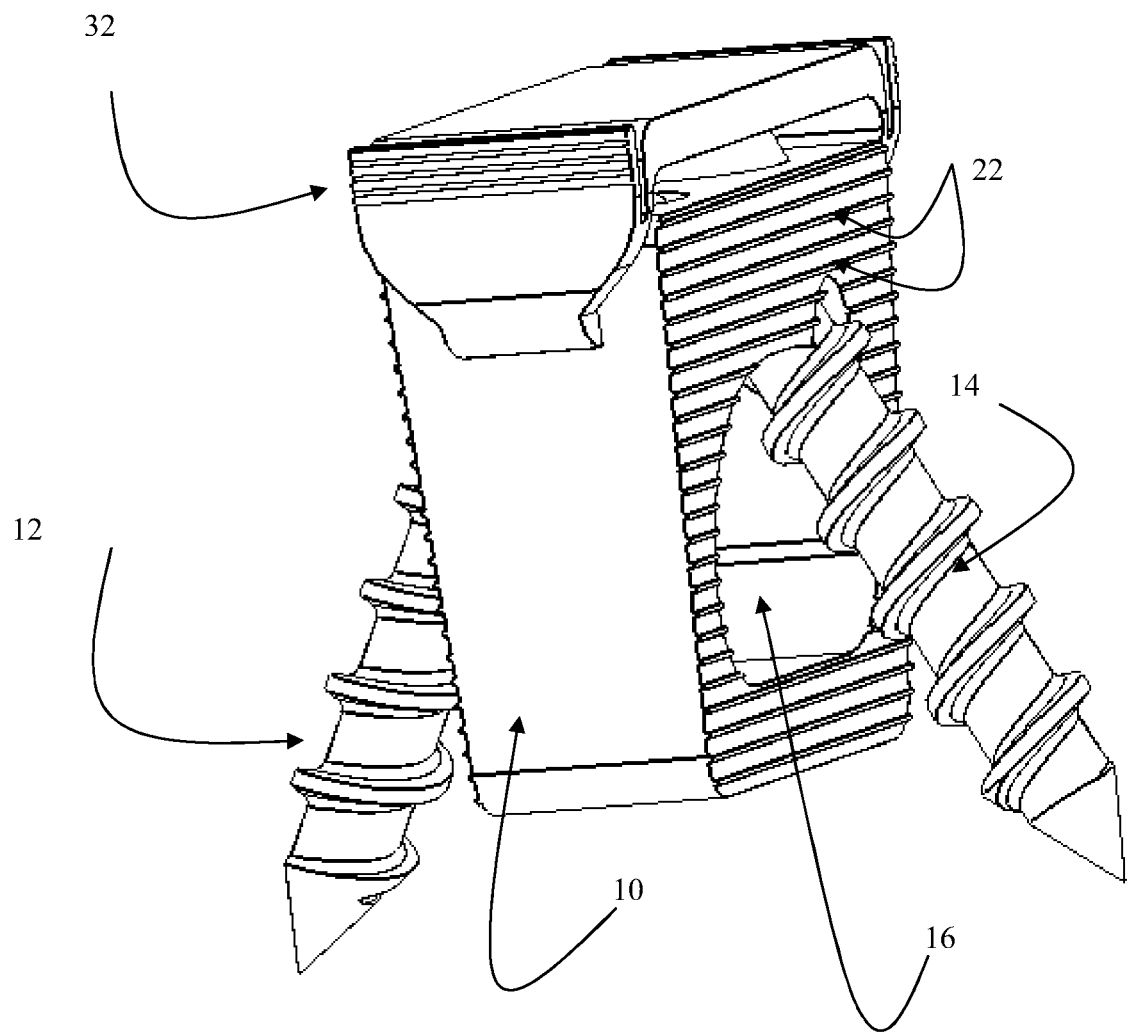
Figure 2D:
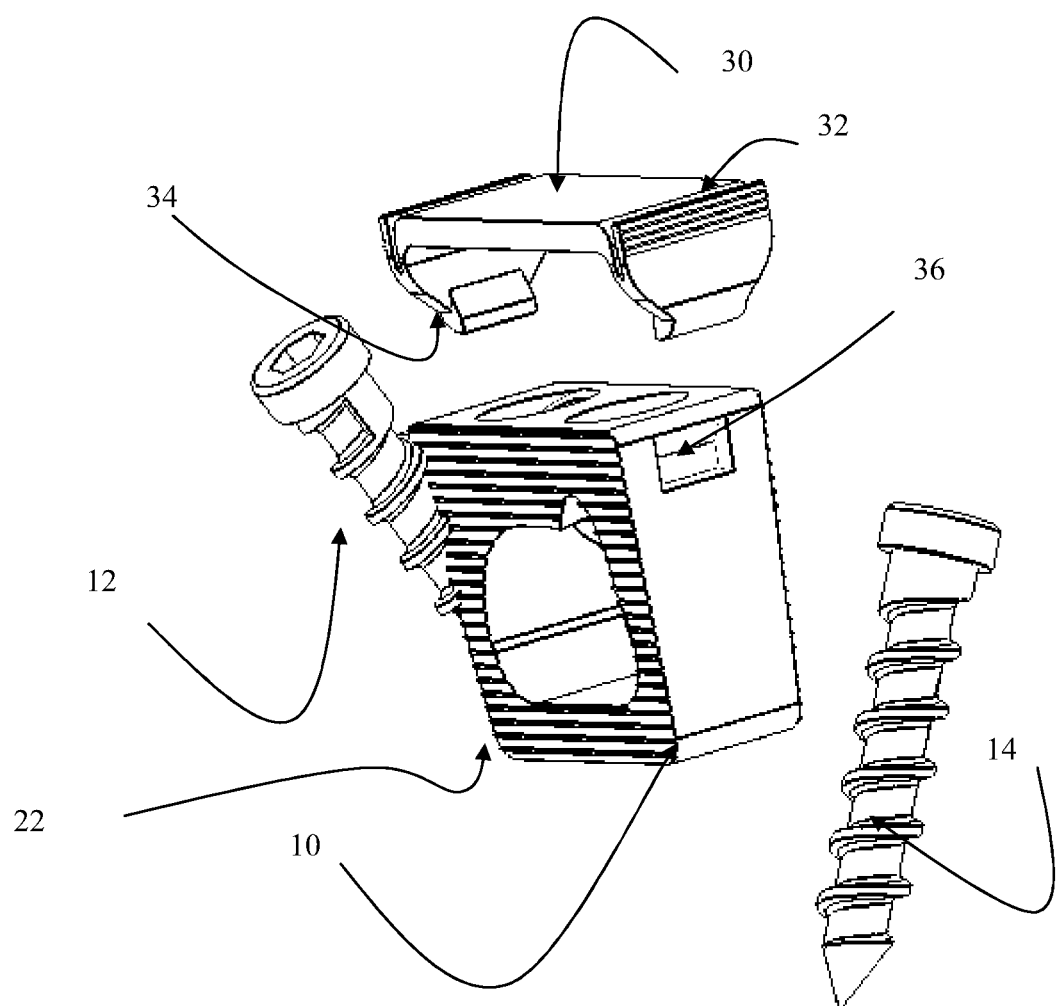
Figure 2E:
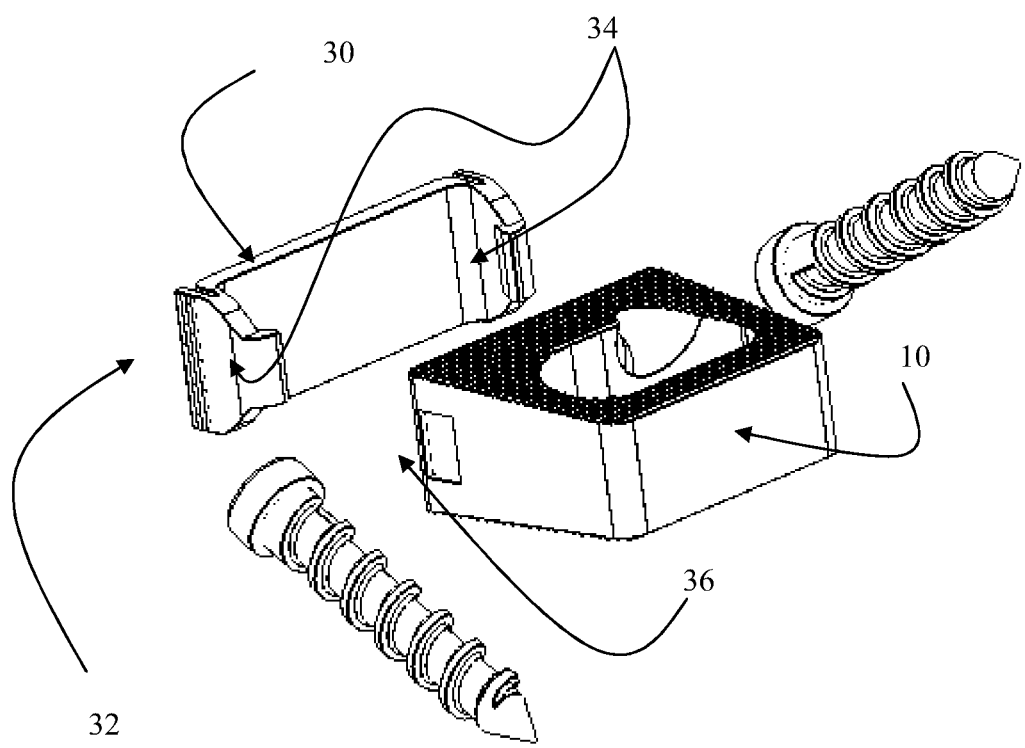

The embodiment also includes a central screw locking lever 24 which is inserted in between left and right internalized screw/drill/guides 18, 20 into the top center of the construct 10 (FIG. 1E). The central screw locking lever 24 can be manufactured from a variety of materials, such as titanium. After the screws 12, 14 are fully turned into the construct 10, the screw locking lever handle 26 which is initially oriented vertically, is rotated ninety degrees so that the handle 26 covers and locks both left and right screws 12, 14 thereby preventing back-out And pull-out. The locking mechanism 24 can be reused for a number of cycles. This locking mechanism 24 is an additional evolutionary embodiment not described in the aforementioned related applications.

For example, an aspect of the invention is directed to bi-directional fixating transvertebral (BDFT) screw/cage 10 apparatus, comprising an intervertebral cage 10 for maintaining disc height, the intervertebral cage 10 including a first internal screw guide 18 and a second internal screw guide 20, a first screw member 12 having a tapered end and a threaded body disposed within the intervertebral cage 10, a second screw member 14 having a tapered end and a threaded body disposed within the intervertebral cage 10, wherein each of the first internal screw guide 18 and the second internal screw guide 20 are angled to orient the first screw member 12 and the second screw member 14 bi-directionally in opposite directions, wherein the first internal screw guide 18 and the second internal screw guide 20 are aligned along a longitudinal axis of the intervertebral cage 10, and a central screw locking lever 24 coupled to the intervertebral cage 10, wherein the central screw locking lever 24 prevents the first screw member 12 and the second screw member 14 from pulling-out of the first internal screw guide 18 and the second internal screw guide 20.

The central screw locking lever 24 can be rotatably coupled to the intervertebral cage 10. The central screw locking lever 24 can include a handle portion 26, and a stem portion 28 extending from a lower side of the handle portion 26, the stem portion 28 being substantially perpendicular to the lower side of the handle portion 26. The central screw locking lever 24 can be rotatable about an axis of the stem portion 28.

The central screw locking lever 24 can be rotatable between an unlocked position in which the handle portion 26 is transverse to the longitudinal axis of the intervertebral cage 10, and a locked position in which the handle portion 26 extends along the longitudinal axis of the intervertebral cage 10.

The first screw member 12 and the second screw member 14 are exposed when the handle portion 26 is in the unlocked position, and the handle portion 26 of the central screw locking lever 24 covers and locks the first screw member 12 and the second screw member 14 in the intervertebral cage 10 when the handle portion 26 is in the locked position. The central screw locking lever can be a T-shaped screw locking lever 24. A top face of the intervertebral cage 10 can include an opening for engaging the central screw locking member 24. The opening 29 can be formed between the first internal screw guide 18 and the second internal screw guide 20. The central screw locking lever 24 can include a first threaded portion and the opening 29 can include a corresponding second threaded portion, and wherein the central screw locking lever 24 is threaded into the opening 29 of the intervertebral cage 10 by engaging the first threaded portion of the central screw locking lever 24 with the second threaded portion of the opening. The central screw locking lever 24 can be press-fit into the opening 29 of the intervertebral cage 10. The central screw locking lever 24 can be made of titanium.

FIGS. 2A-E depict another screw locking mechanism for anterior cervical cage/BDFT constructs. This locking mechanism is a screw locking horizontal bracket 30 which snaps on to the top of the construct 10 once the screws 12, 14 have been maximally turned thereby preventing screw pull-out or back-out. The screw locking bracket 30 is designed with left and right bracket hooks 34. They are inserted into hook insertion slots 36 which are prefabricated on the left and right sides of the cage construct 10 to precisely snugly fit the bracket hooks 34. Once the bracket hooks 34 are inserted into the cage insertion slots 36, the bracket 30 cannot be dislodged. In order to remove the bracket 30; if it becomes necessary to remove the cage 10 at some future time, flexion grips (side tabs) 32 have been designed on the bracket 30. The locking bracket 30 can be applied to the construct 10 with the specially designed pliers (exemplarily described with reference to FIG. 5) which press fit the bracket 30 onto the cage 10 thereby locking the screws 12, 14. In order to remove the bracket 30, the user needs only to press on the side tabs 32 with the pliers (FIG. 5) to slightly deform (open) the bracket hooks 34, and thereby easily remove the bracket 30.

The novel embodiments of the present invention are quite unique and different from all other conventional locking mechanisms used for other types of anterior cervical plates.

No other conventional anterior cervical intervertebral cage/BDFT screw constructs are known.

For example, an exemplary aspect of the invention is directed to a central screw locking lever 24 can include a screw locking horizontal bracket 30. The screw locking horizontal bracket 30 can be press fit on a top of the intervertebral cage 10 and covers and locks the first screw member 12 and the second screw member 14 in the intervertebral cage 10. The screw locking horizontal bracket 30 can include a cover portion extending in a direction of the longitudinal axis of the intervertebral cage 10 and substantially parallel to a top face of the intervertebral cage 10, the cover portion covering and locking the first screw member 12 and the second screw member 14 in the intervertebral cage 10, and side tabs 32 on each end of the cover portion, wherein the side tabs 32 extend in a direction perpendicular to the cover portion along the sides of the intervertebral cage 10. The side tabs 32 include bracket hooks 34 extending from the side tabs 32 toward the sides of the intervertebral cage 10 and in a direction of the longitudinal axis of the intervertebral cage 10. The intervertebral cage 10 can include one or more slots 36 for lockingly engaging a part of the screw locking horizontal bracket 30. The sides of the intervertebral cage 10 include hook insertion slots 36, and wherein the bracket hooks 34 engage the hook insertion slots 36. The bracket hooks 34 lockingly engage the hook insertion slots 36. The side tabs 32 of the screw locking horizontal bracket 30 include bracket flexion grips. The screw locking horizontal bracket 30 can be deformable. The screw locking horizontal bracket 30 can be deformable under pressure applied to the bracket flexion grips. The bracket hooks 34 include flexible bracket hooks.

Figure 3A:
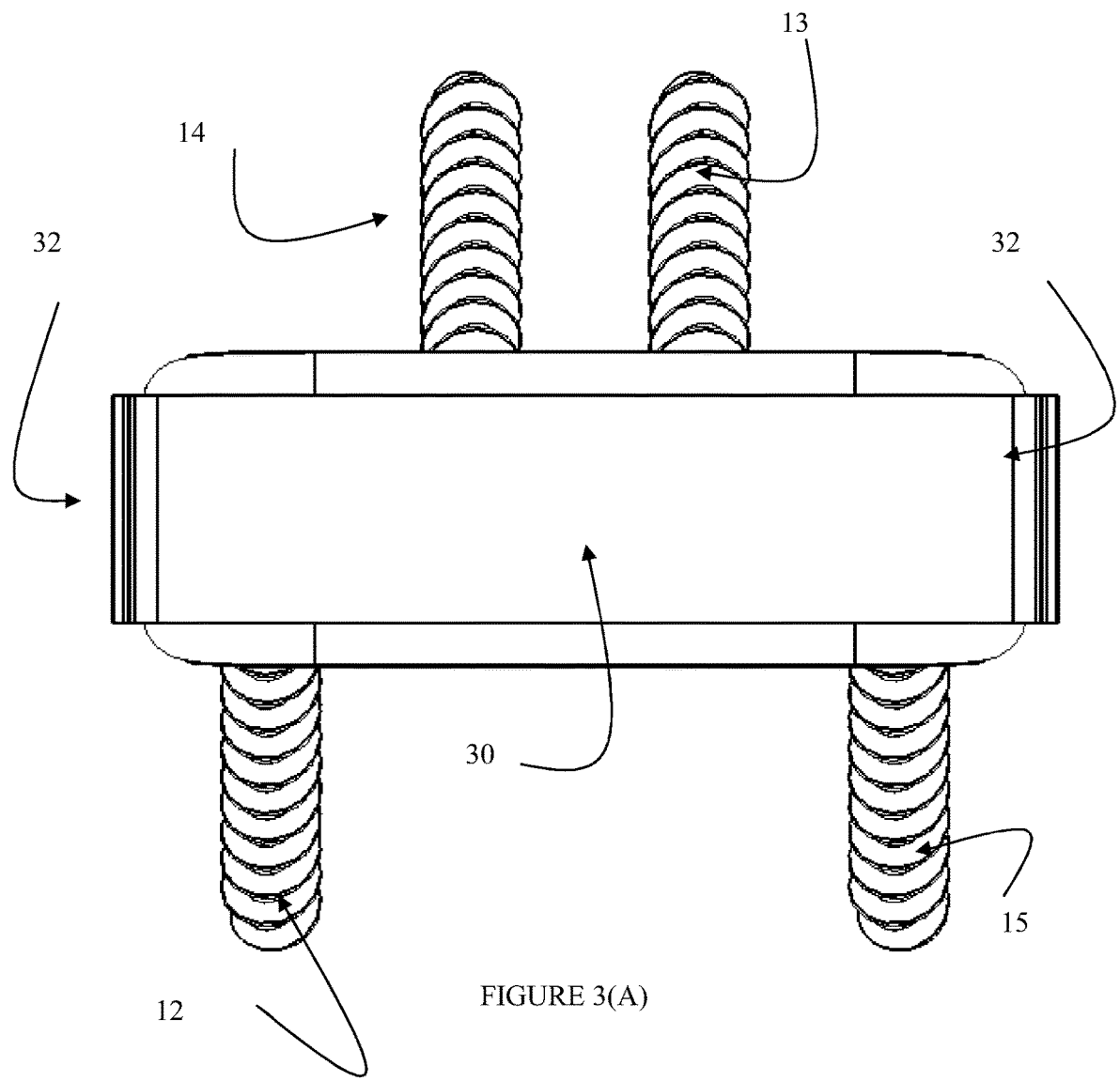
FIGS. 3A-F illustrate an embodiment of an anterior lumbar intervertebral cage/BDFT screw construct with screw locking bracket in top (FIG. 3A), bottom (FIG. 3B), front (FIG. 3C), side (FIG. 3D), isometric top fully exploded with visualized internalized angled screw guides (FIG. 2E), and isometric fully exploded with visualized bracket hooks and flexion grips (FIG. 3F) views.
Figure 3B:
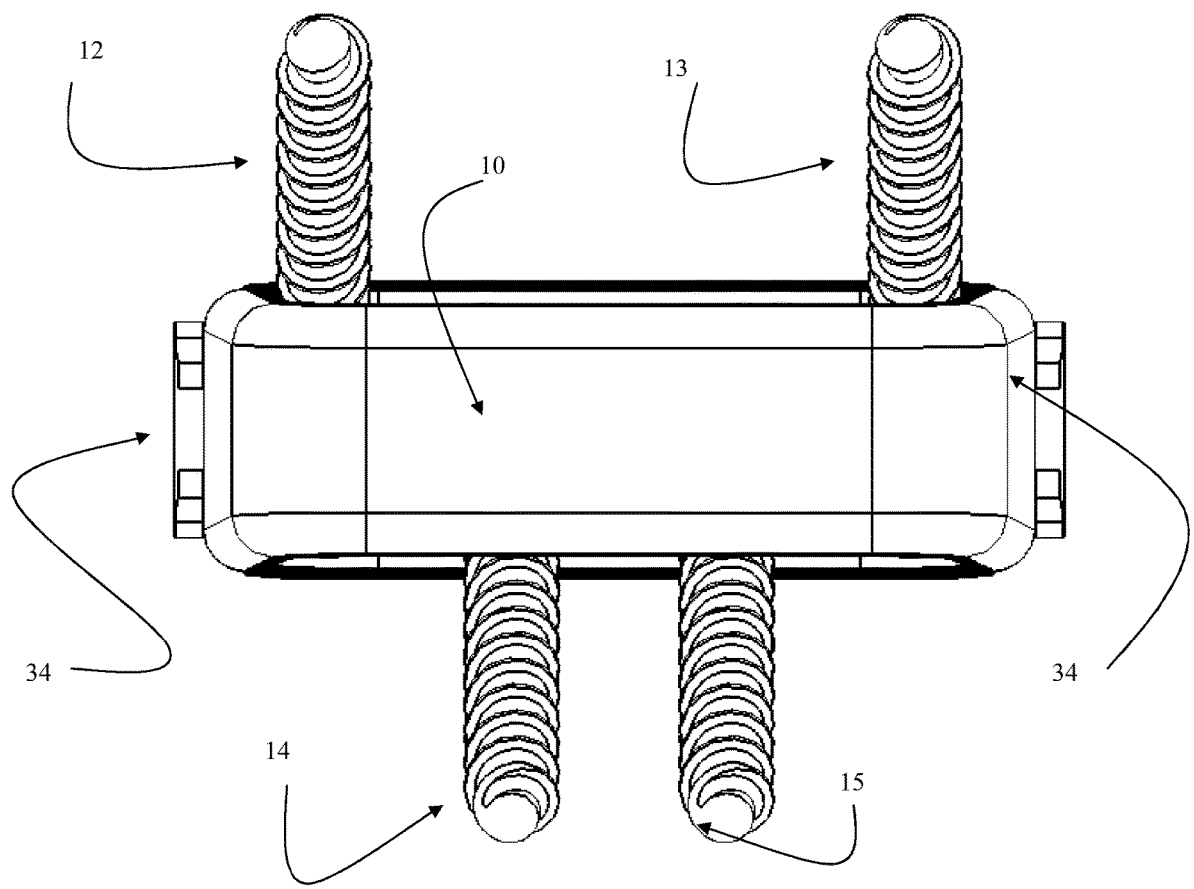
Figure 3C:
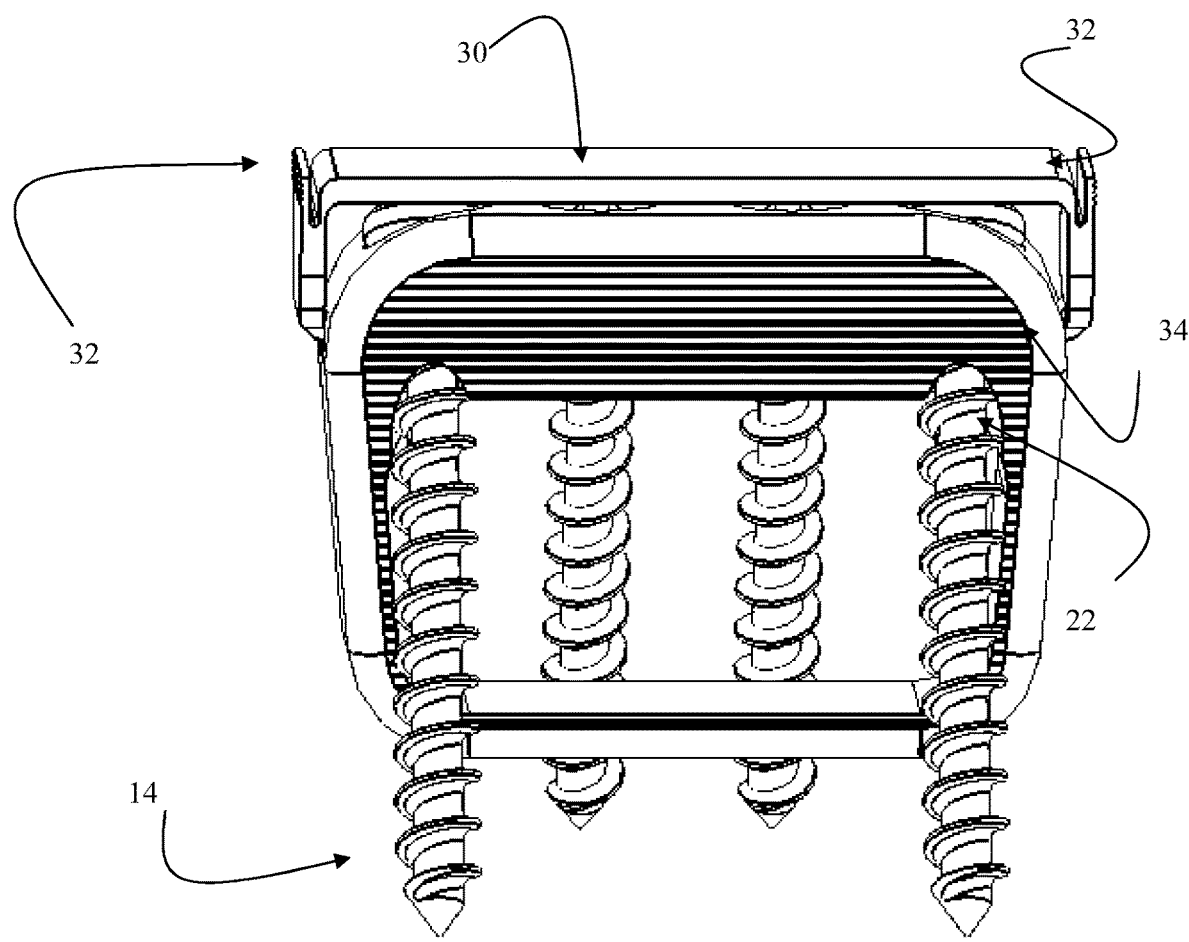
Figure 3D:
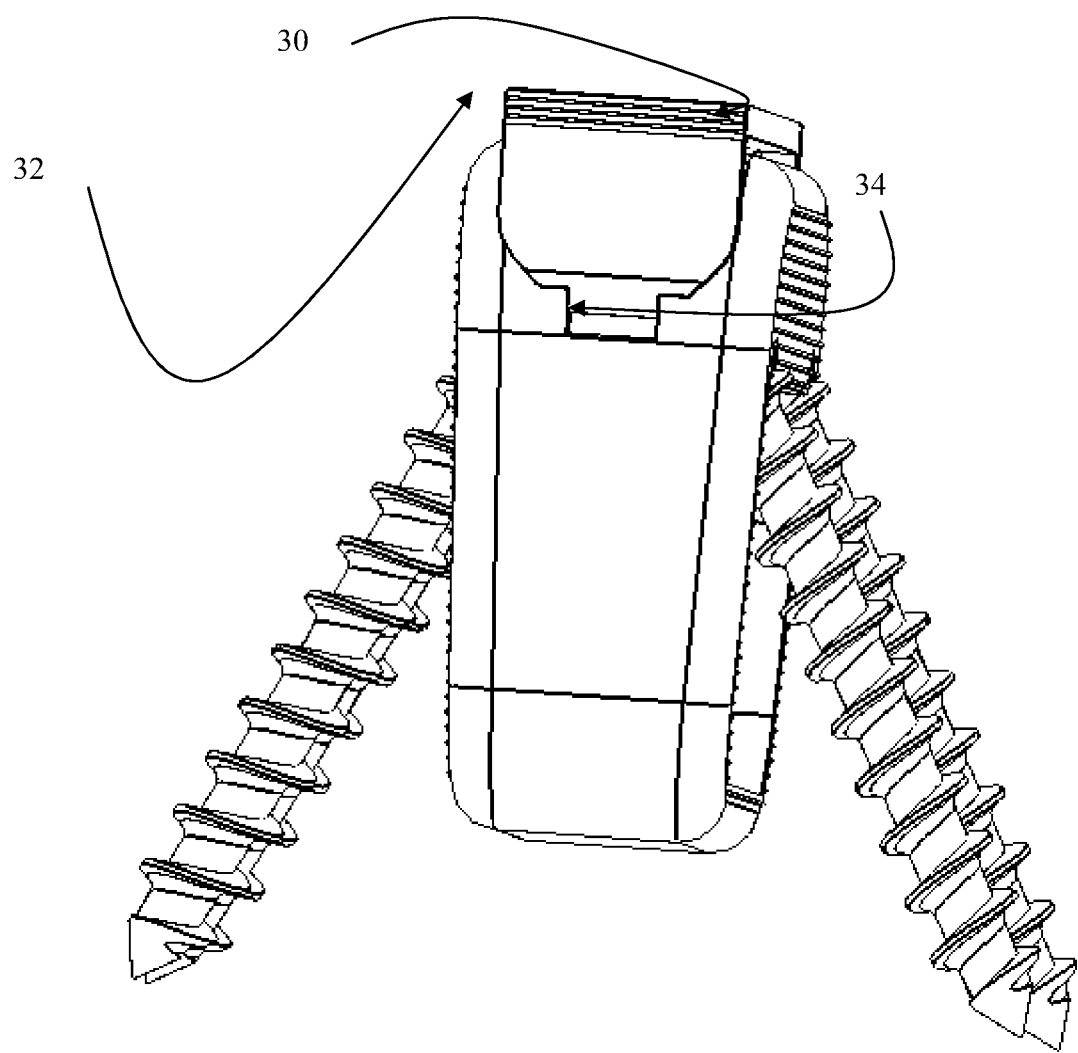
Figure 3E:
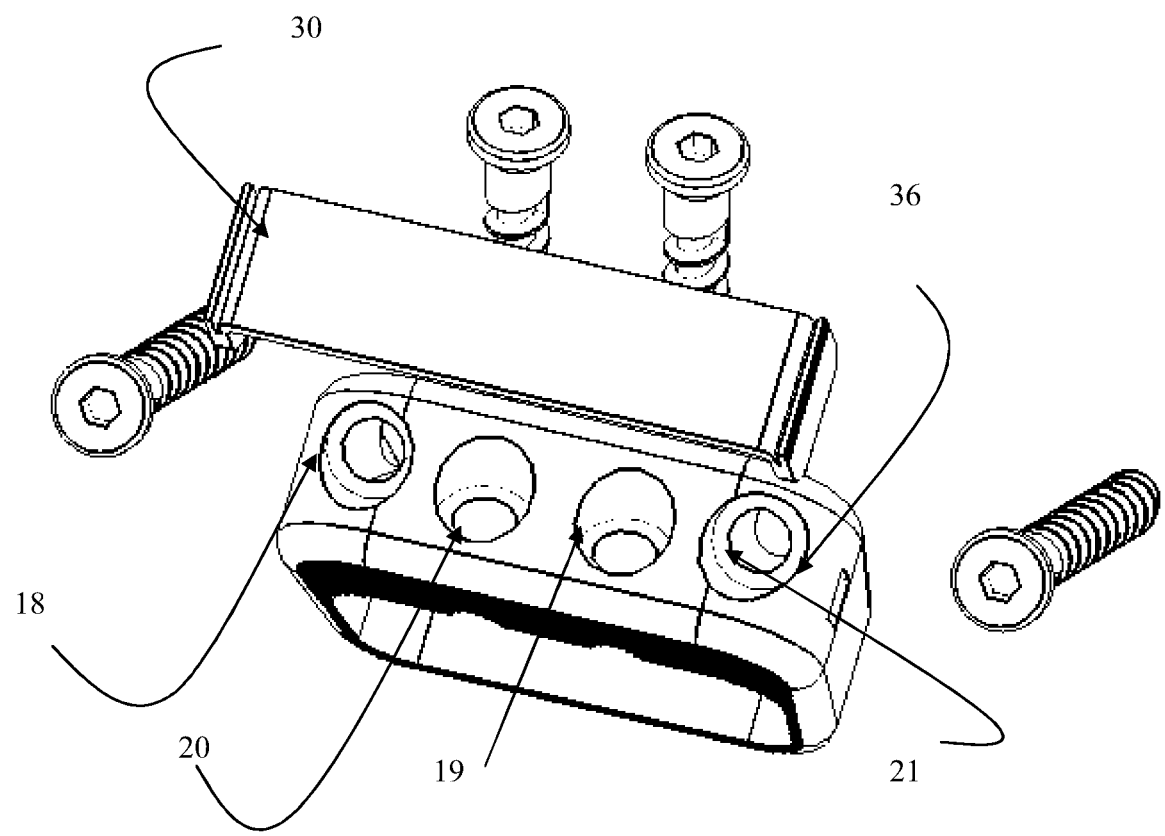
Figure 3F:
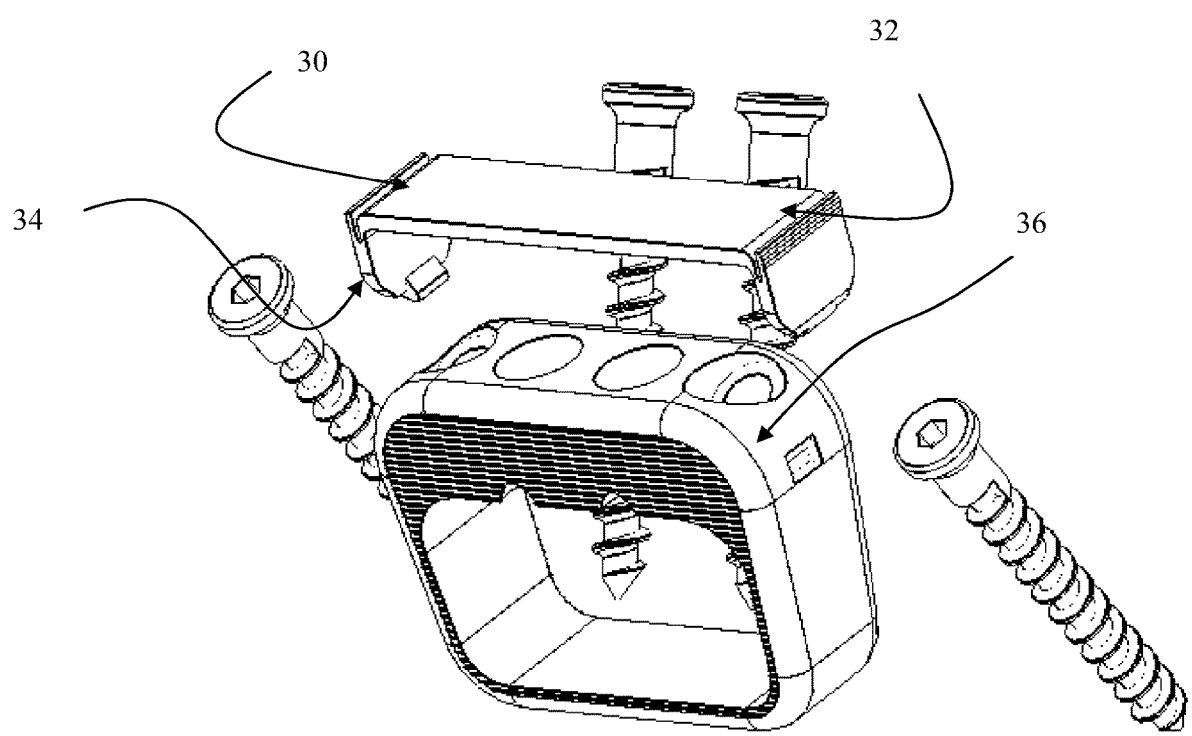

FIGS. 3A-F illustrate three-dimensional views of an embodiment of an anterior lumbar intervertebral cage/BDFT construct. In this embodiment, the cage 10 is larger than the cervical cage and is also elliptically contoured to fit into the bi-concave lumbar disc space (FIG. 3D; side view). The cage 10 includes four (4) horizontally aligned internalized screw guides 18, 19, 20, 21 for four (4) screws 12, 13, 14, 15. The two lateral (left and right) screws are oriented inferiorly, and the two middle screws are oriented superiorly. In the embodiment, the orientations of the four screw guides 18, 19, 20, 21 (and screws 12, 13, 14, 15) are selected because of their symmetry and inherent stability. The cage 10 can include a large cavity 16 for bone product placement. The cage 10 includes four built-in internalized screw/drill guides 18, 19, 20, 21, one for each screw. Other embodiments of the intervertebral cage 10 can be designed with internalized screw/drill guides 18, 19, 20, 21 with different angles and/or different positions within the cage 10. The angle and size of the screws make them amenable to single or multi-level placement. The superior and inferior surfaces or edges of the cage 110 can include ridges 22 to facilitate integration and fusion with superior and inferior vertebral bodies. In this embodiment, there are no compartmental divisions in the cavity 16 for bone product placement to maximize the quantity of bone for fusion.

FIGS. 3A-F depicts a screw locking embodiment for anterior thoracic and Lumbosacral cage/BDFT constructs. This locking mechanism is a screw locking horizontal bracket 30 which snaps on to the top of the construct once the four screws 12, 13, 14, 15 have been maximally turned thereby preventing screw pull-out or back-out of all four screws 12, 13, 14, 15 simultaneously. The screw locking bracket 30 is designed with left and right bracket hooks 34. They are inserted using the specially designed pliers (FIG. 5) into hook insertion slots 36 which are prefabricated on the left and right sides of the cage construct to precisely snugly fit the bracket hooks 34. Once the bracket hooks 34 are inserted into the cage insertion slots 36, the bracket 30 cannot be dislodged. In order to remove the bracket 30; if it might become necessary to remove the cage 10 at some future time, flexion grips (side tabs) 32 have been designed on the bracket 30. The locking bracket 30 is the press fit by the pliers (FIG. 5) onto the cage 10 in order to lock the screws 12, 13, 14, 15. In order to remove the bracket 30, the user needs only to press on the side tabs 32 with the pliers (FIG. 5) to slightly deform (open) the bracket hooks thereby easily removing the bracket 30.

Another identical locking mechanism embodiment which includes a central rotating locking lever mechanism as designed for the cervical cage. BDFT constructs can likewise be designed for the anterior thoracic and lumbosacral cage/BDFT constructs. These novel locking mechanisms also are quite unique and different from all other conventional locking mechanisms used for other types of anterior lumbar cages.

Another patent which mentions anterior placed lumbar implants with perforating screws includes U.S. Pat. No. 4,904,261 (John Dove, Philip H. Hardcastle, John K. Davis and Brian King). The '261 patent discloses a horseshoe implant having a plurality of cylindrical holes with smooth inner surfaces and comprise only one stop for the heads of the bone screws to be inserted into them. The placement of five cylindrical holes is oriented within the cage in a non-symmetric manner.

In comparison, the embodiments of the present invention differ in many substantial ways from the conventional devices. For example, the present invention provides a symmetric orientation of the screw holes, as well as completely novel and unique screw locking mechanism (e.g., 24, 30, etc.). The present invention also describes an angulation/trajectory (e.g., a preferred angulation/trajectory) for preventing pull-out or back-out of the screws that would make placement of all screws in a manner which would lead to maximum stability of the construct within the vertebral space, and obviate the need for external drill guides, and surgeon trajectory angulation guess work.

In another patent U.S. Pat. No. 7,232,464 B2 (Claude Mathieu and Christopher Marden John Cain) multiple embodiments of lumbar intervertebral implants are presented which include one with internally threaded bore holes, another embodiment with a front plate mounted at the front surface of the implant, and another embodiment with the front place displaceably configured to move vertically relative to the implant. In addition, the disclosed preferred borehole axes are 35-55 degrees. The '464 patent has four screw perforations that are not aligned four in a row. Two of the screw holes are laterally placed on the left, one on top of each other, the top one with a superior trajectory, and the bottom with an inferior trajectory. Likewise, two perforations are placed on the right, one on top of each other, the top one with a superior trajectory and the bottom one with an inferior trajectory. The disclosed screw locking mechanism is a screw with an external thread matching the internal borehole thread, or spiral springs.

In comparison, the anterior lumbar construct of the present invention differs in many substantial ways from the conventional devices. The present invention includes a single cage construct with four (4) internalized drill guides 18, 19, 20, 21 arranged horizontally in a row. The middle two screws are oriented superiorly, and the lateral left and right screws are oriented inferiorly. This symmetric alignment of screws and orientations within the superior and inferior vertebral bodies (e.g., two middle superiorly projecting screws, and two laterally projecting inferior screws) make the fixation to the superior and inferior vertebral bodies much more symmetric and thus more stable. In an embodiment of the present invention, the cage includes a screw guide having a predetermined trajectory (e.g., a preferred trajectory of 25 degrees) that makes placement of all screws equally facile, more amenable to multi-level placement, and diminishes the need for external drill guides. Furthermore, the exemplary screw locking mechanisms are unique and differ substantially from the conventional approach of matching screw/cage threads or spiral springs.

Figure 4A:
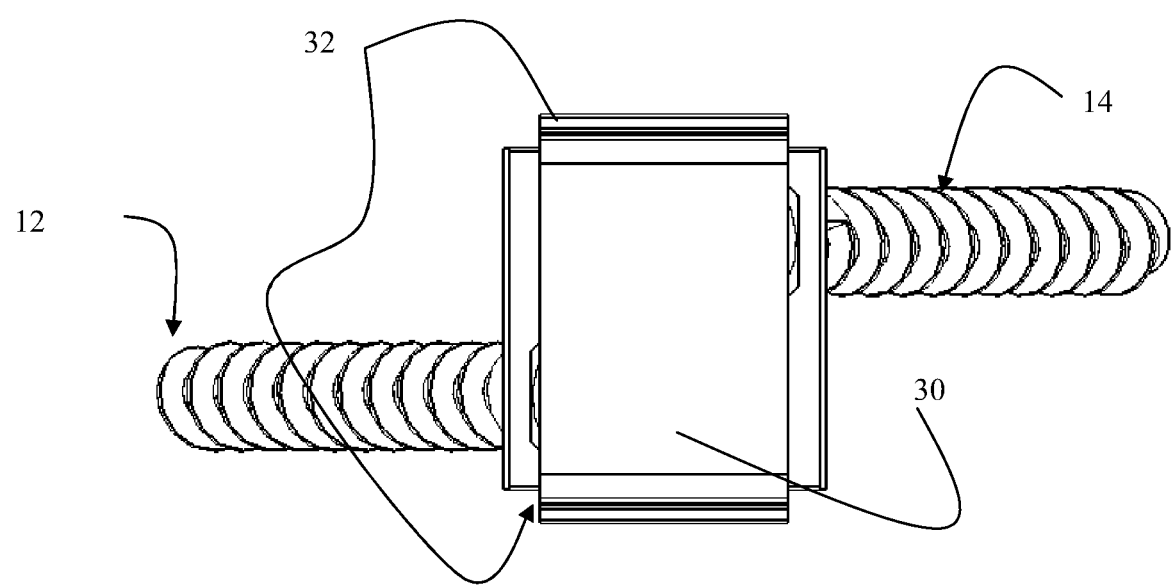
FIGS. 4A-F illustrate an embodiment of a posterior lumbar intervertebral cage/BDFT construct with screw locking bracket in top (FIG. 4A), front (FIG. 4B), side (FIG. 4C), isometric (FIG. 4D), isometric fully exploded with visualized internalized angled screw guides (FIG. 4E), and isometric fully exploded with visualized bracket hooks and flexion grips (FIG. 4F) views.
Figure 4B:
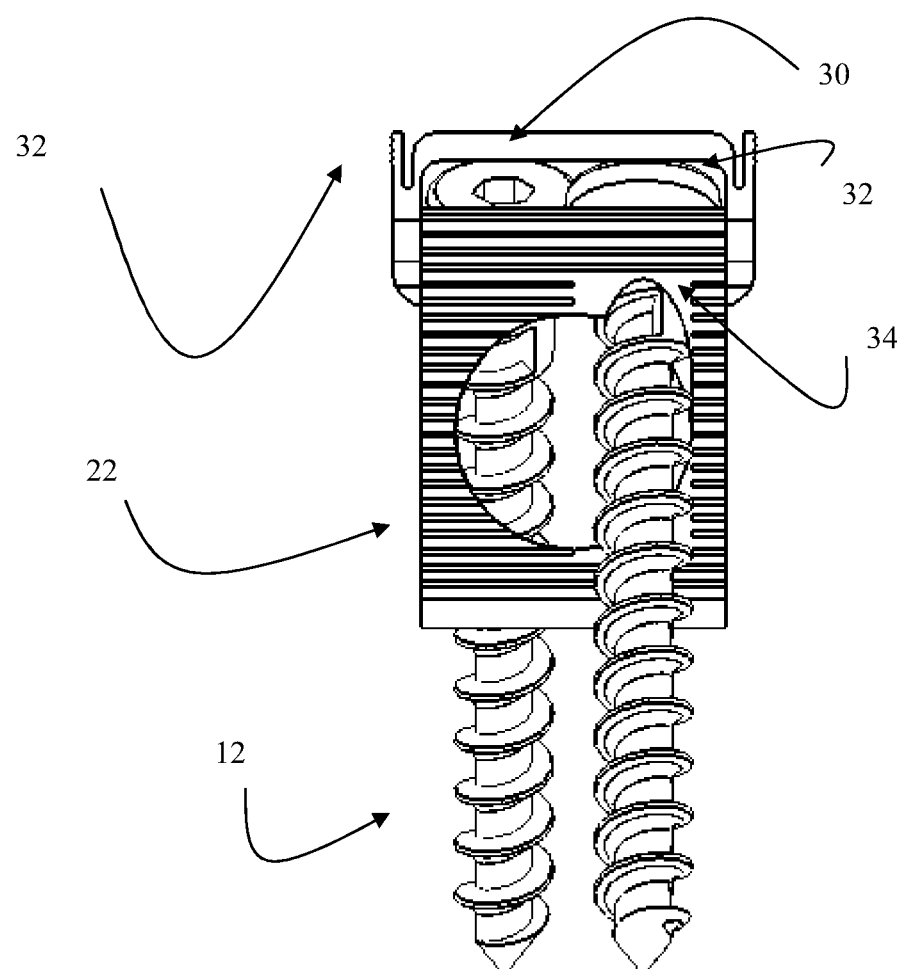
Figure 4C:
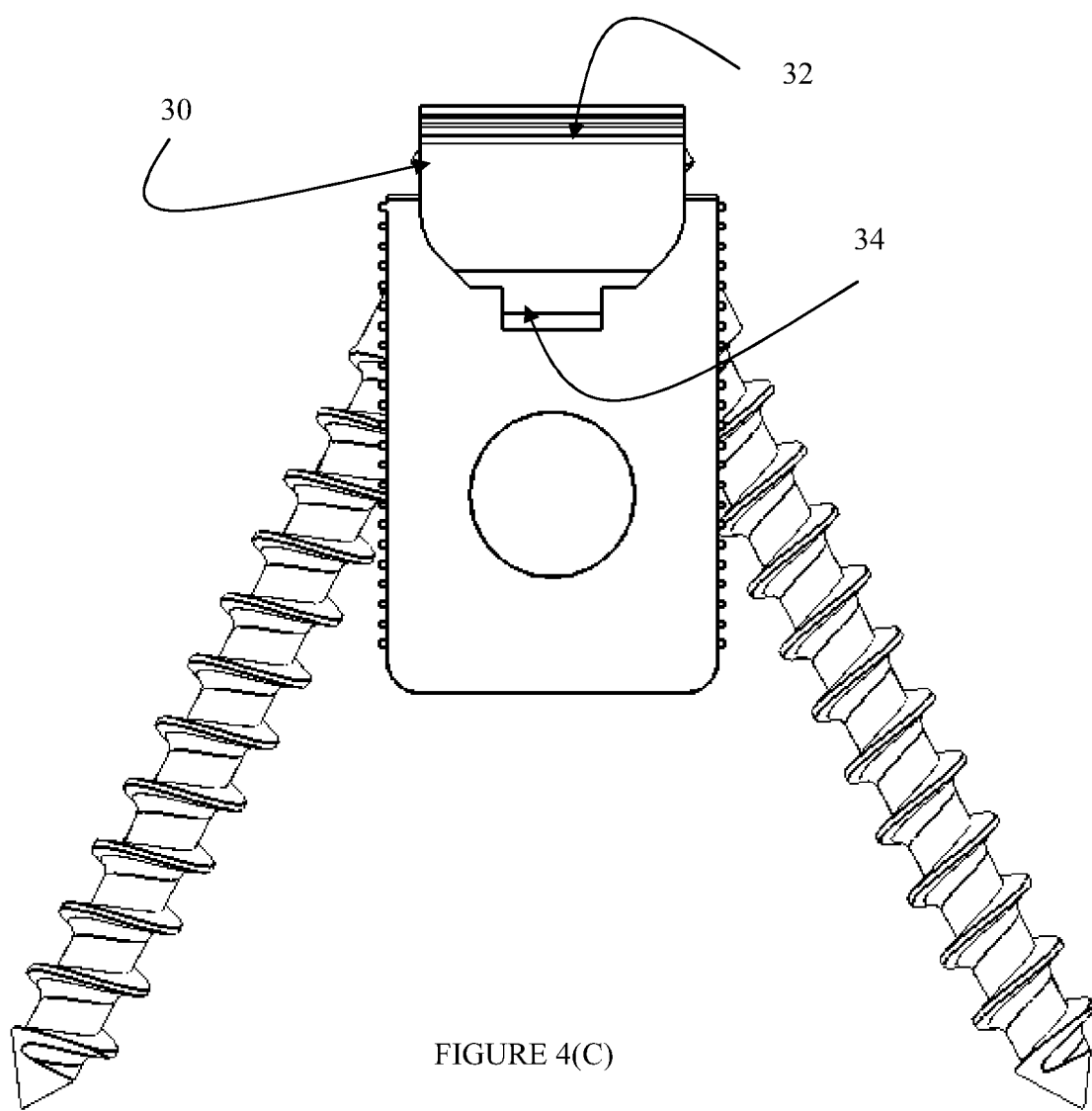
Figure 4D:
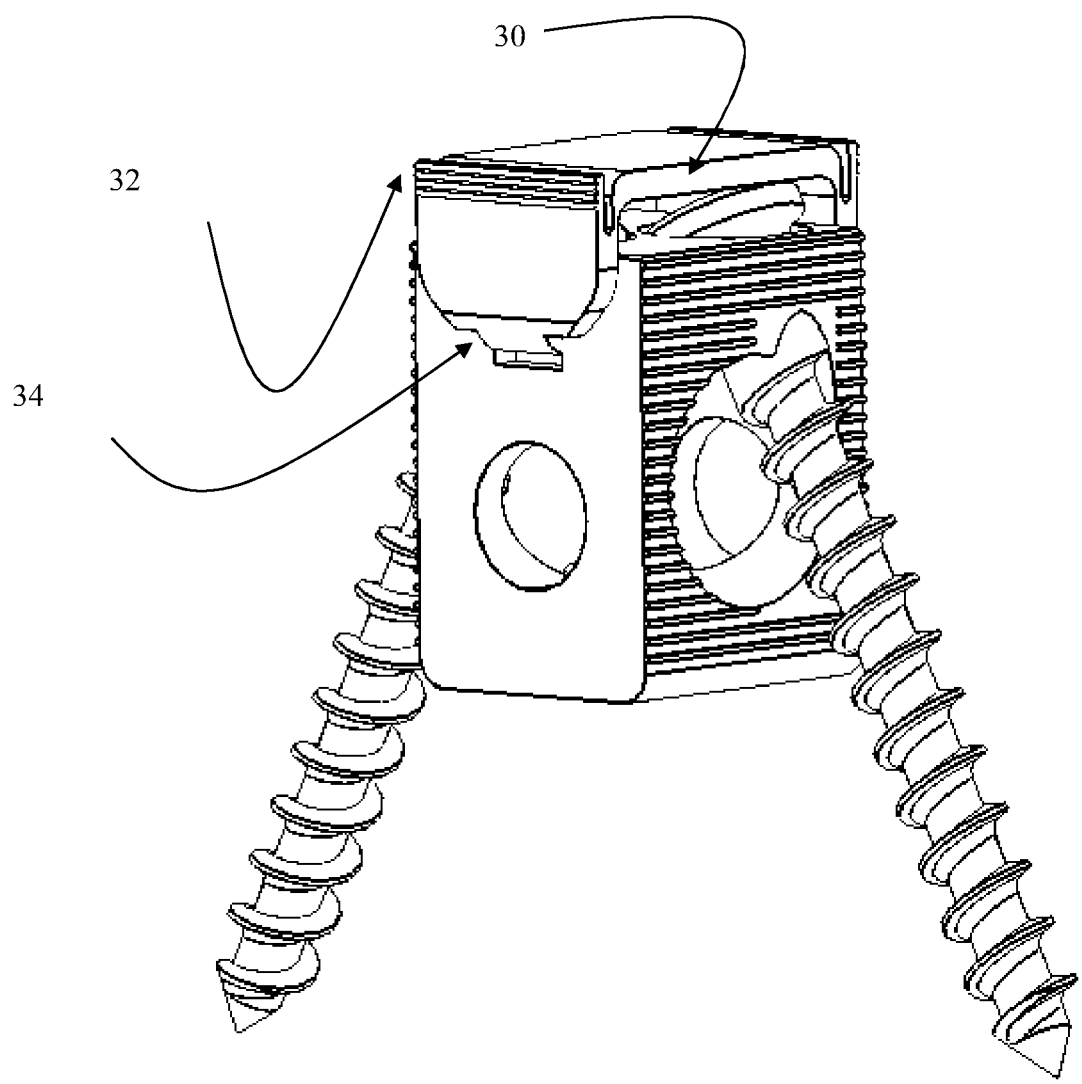
Figure 4E:
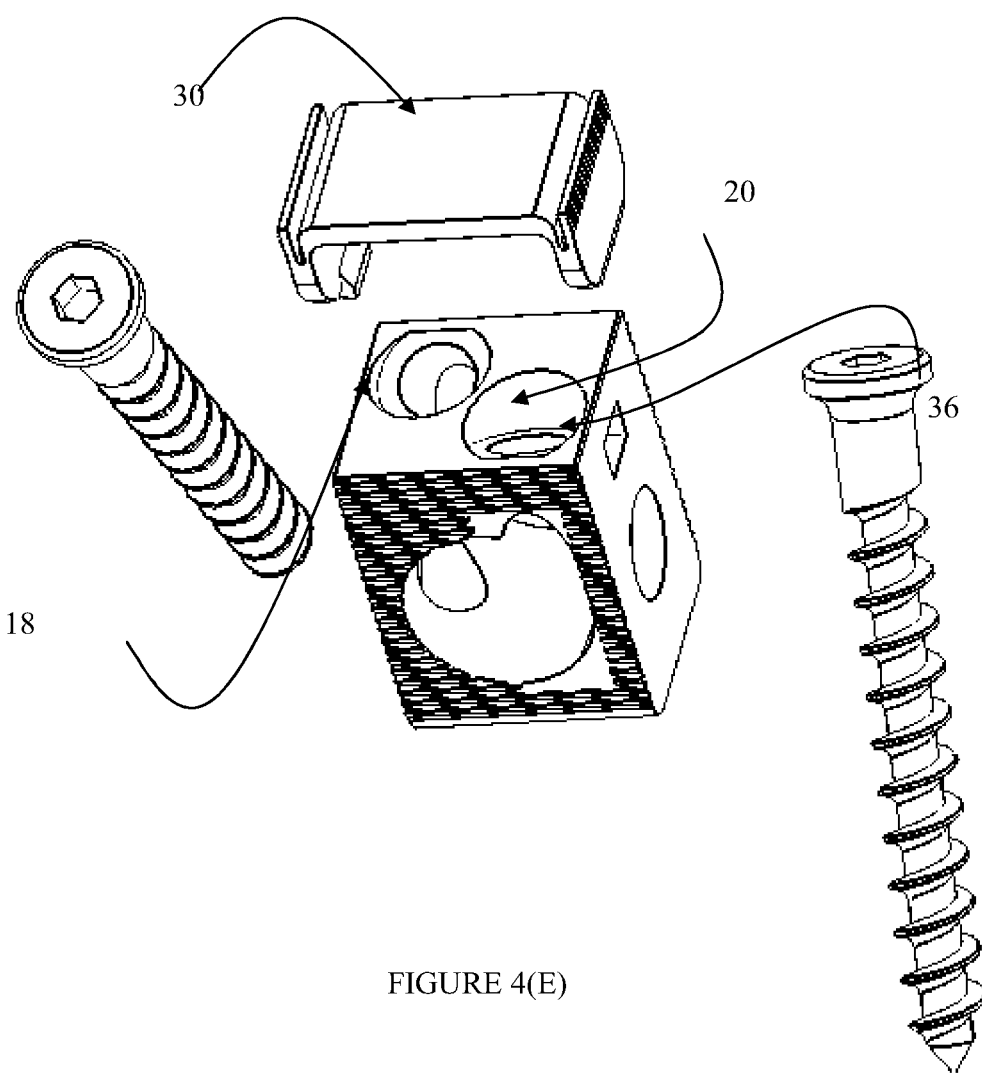
Figure 4F:
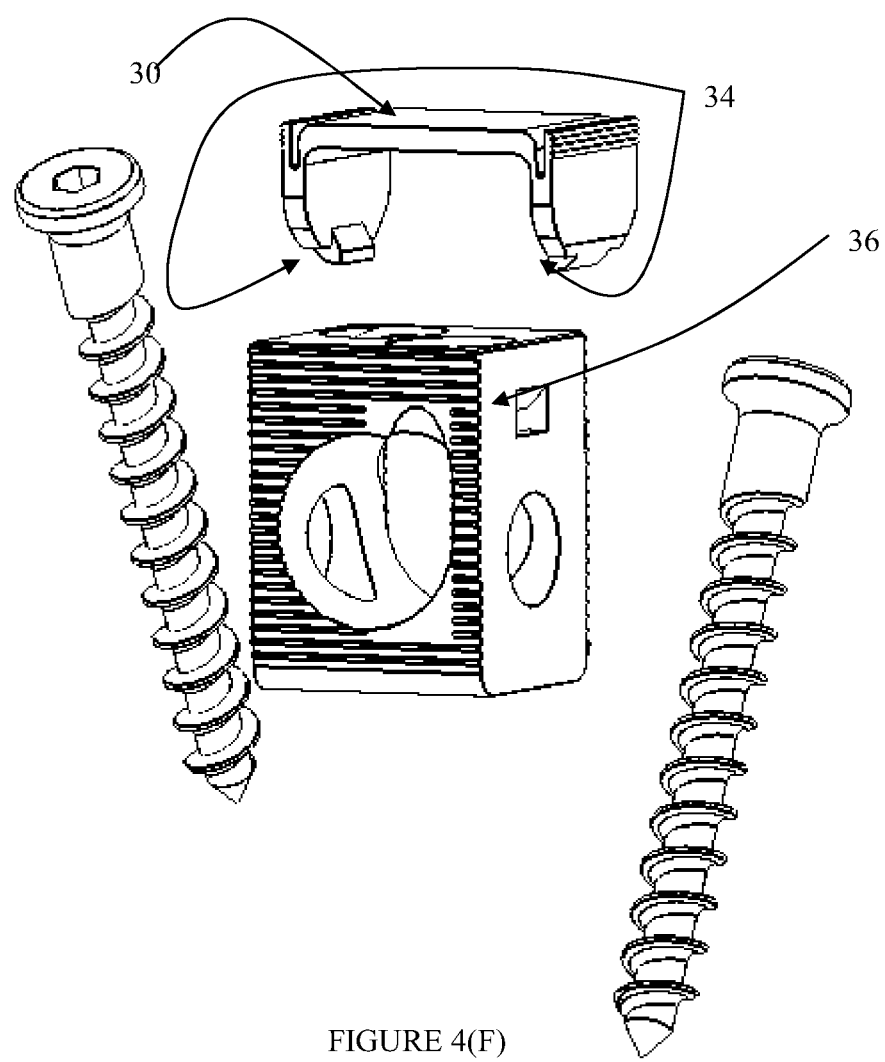

FIGS. 4A-F illustrate three-dimensional views of an embodiment of a posterior lumbar intervertebral cage/BDFT construct. In this embodiment, the screws perforate and orient in opposing superior and inferior directions. The cage 10 can include a cavity 16 for bone product placement. The top and bottom portions of the cage 10 are elliptically contoured to naturally fit into the bi-concave intervertebral disc space (FIG. 4C; side view). The cage 10 includes built-in internalized screw/drill guides 18, 19 having a predetermined angled trajectory. One of the guides is angled rostrally (superiorly) (e.g., guide) and the other caudally (inferiorly) (e.g., guide). The intervertebral cages can be designed with internalized screw/drill guides 18, 19 with different angles and/or different positions within the cage 10. The angle and size of the screws 12, 14 make them amenable to single or multi-level placement. The superior and inferior surfaces or edges can include ridges 22 to facilitate integration and fusion with superior and inferior vertebral bodies. One of these constructs is placed posteriorly into the intervertebral space on the left side, and the other on the right side.

The cage 10 includes a screw locking mechanism for posterior lumbosacral cage/BDFT constructs. This locking mechanism is a screw locking horizontal bracket 30 which snaps on to the top of the construct once the screws have been maximally turned thereby preventing screw pull-out or back-out. The screw locking bracket 30 is designed with left and right bracket hooks 34. They are inserted into hook insertion slots 36 which are prefabricated on the left and right sides of the cage construct to precisely snugly fit the bracket hooks 34. Once the bracket hooks 34 are inserted into the cage insertion slots 36 using the specially designed pliers (FIG. 5), the bracket 30 cannot be dislodged. In order to remove the bracket 30; if it becomes necessary to remove the cage 10 at some future time, flexion grips (side tabs) 32 have been designed on the bracket 30. The locking bracket 30 can be press fit onto the cage 10 using the pliers (FIG. 5) thereby locking the screws 12, 14. In order to remove the bracket 30, the user needs only to press on the side tabs 32 with the pliers (FIG. 5) to slightly deform (open) the bracket hooks 34, and thereby easily remove the bracket 30.

The screw locking bracket 30 can be manufactured from a variety of materials, such as titanium. It can be reused for a number of cycles.

Figure 5:
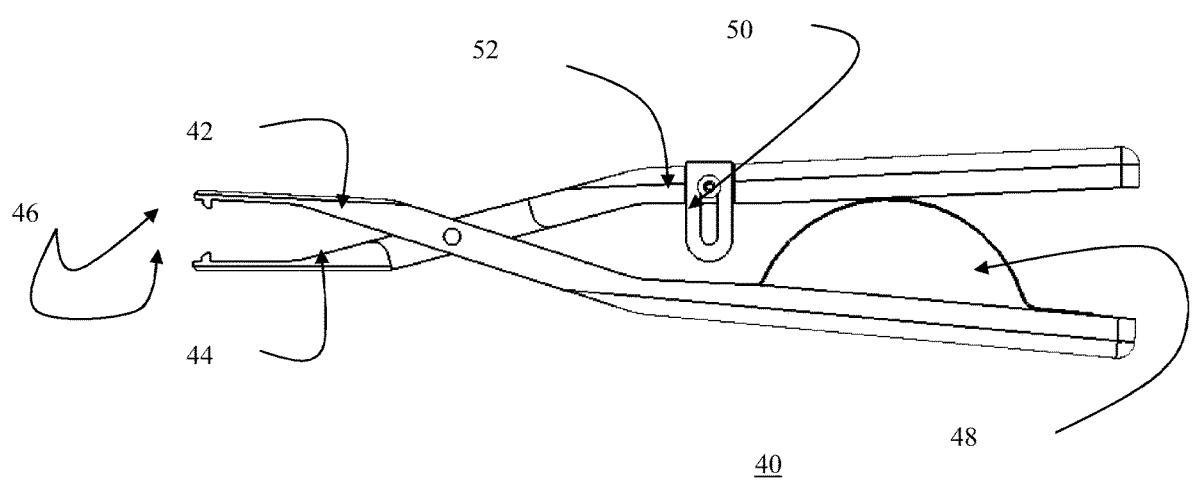
FIG. 5 illustrates a pliers embodiment which applies the locking bracket to and also removes it from the intervertebral cage/BDFT constructs.
Figure 6A:
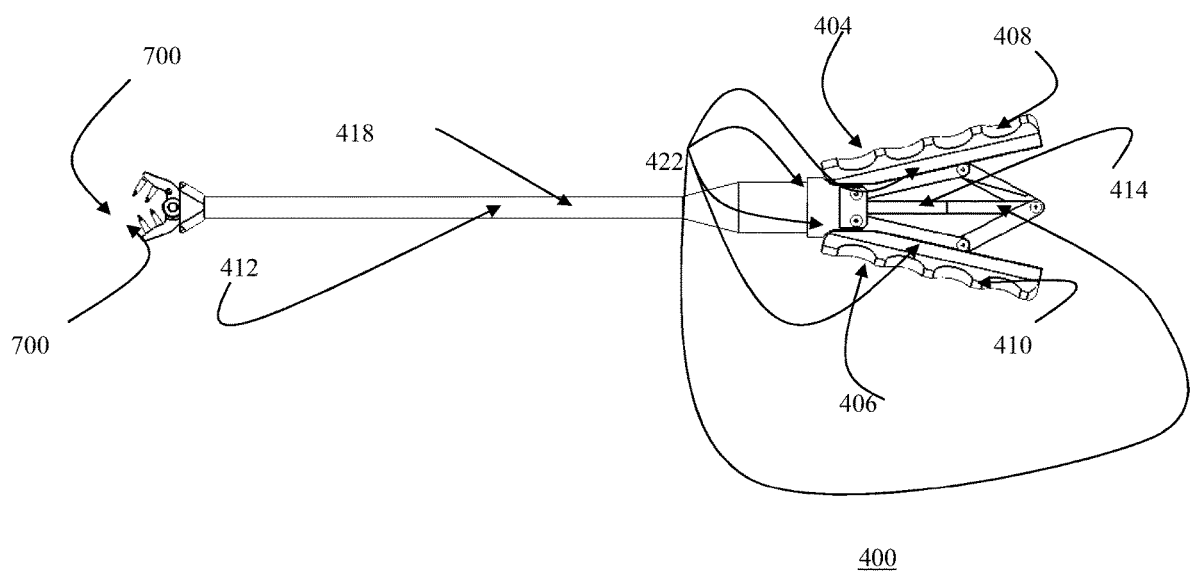
FIGS. 6A-D illustrate an embodiment of a Lumbar facet joint staple gun in side view (FIG. 6A), exploded (FIG. 6B) and cross-sectional (FIG. 6C) and front-on (FIG. 6D) view.
Figure 6B:
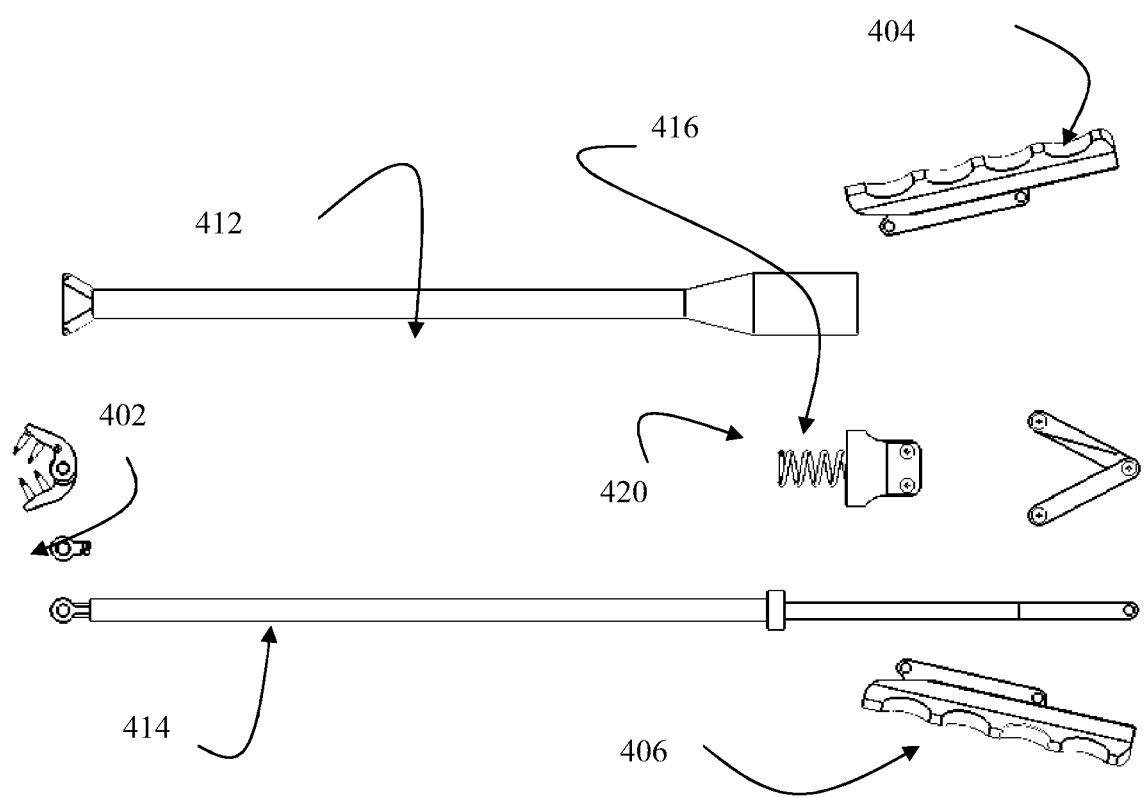
Figure 6C:
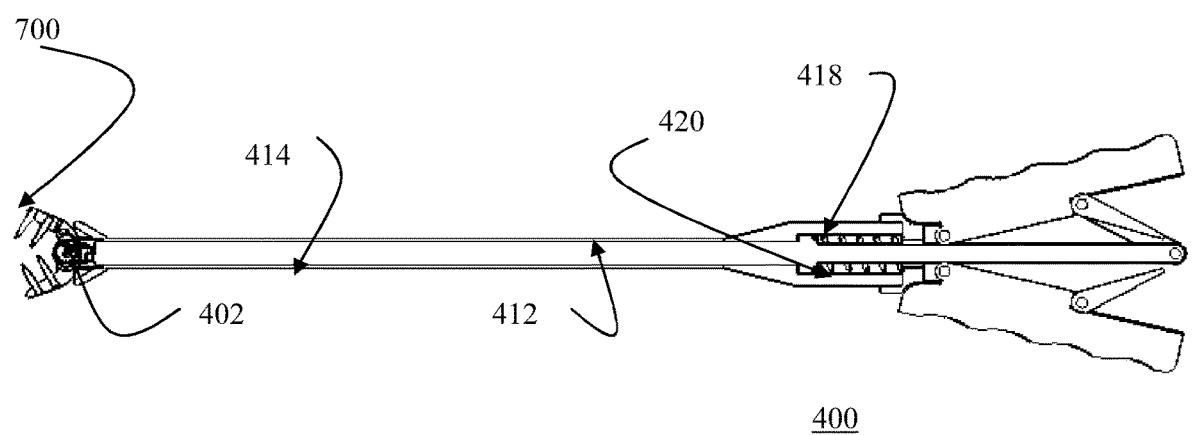
Figure 6D:
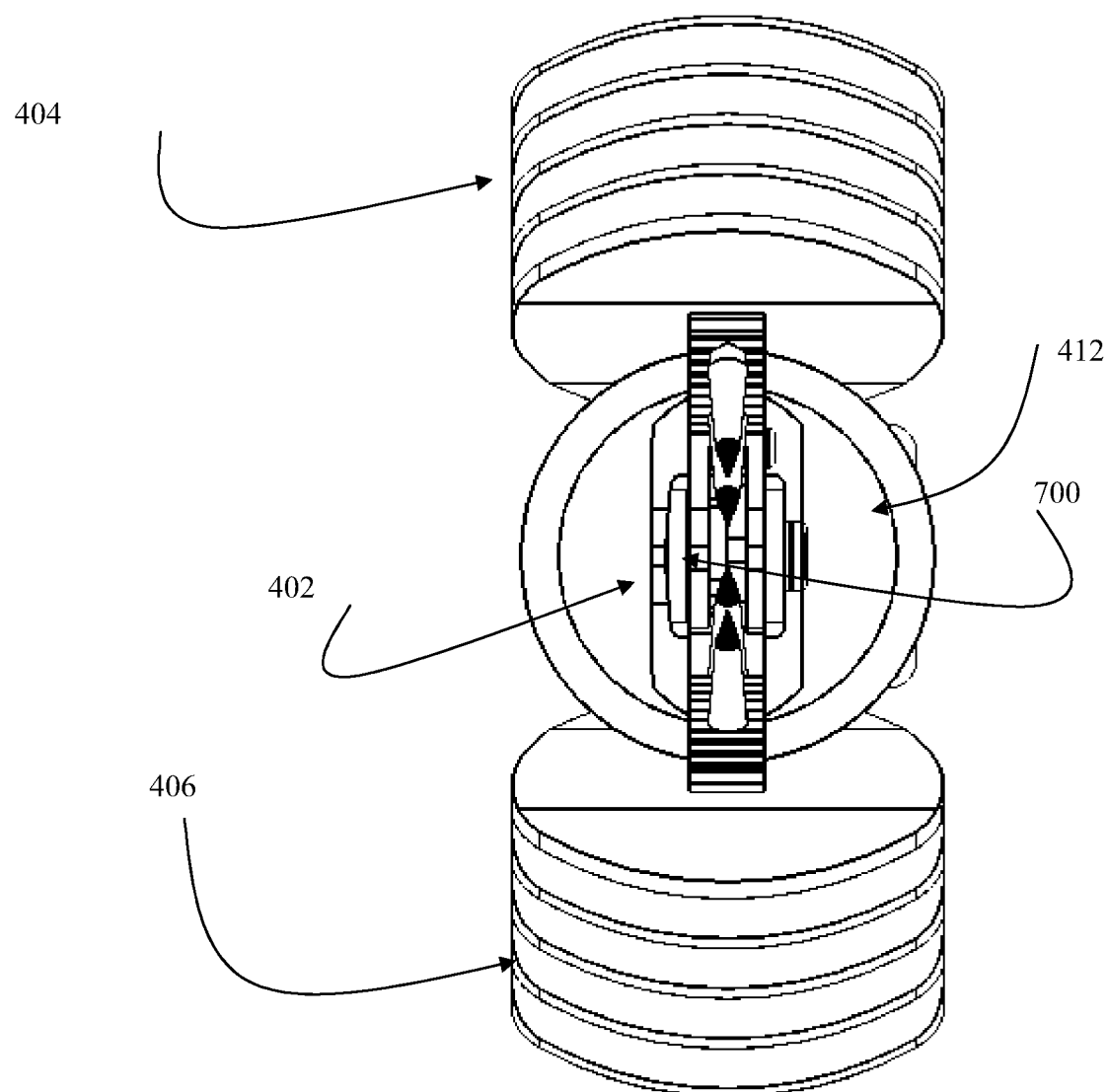
Figure 7A:
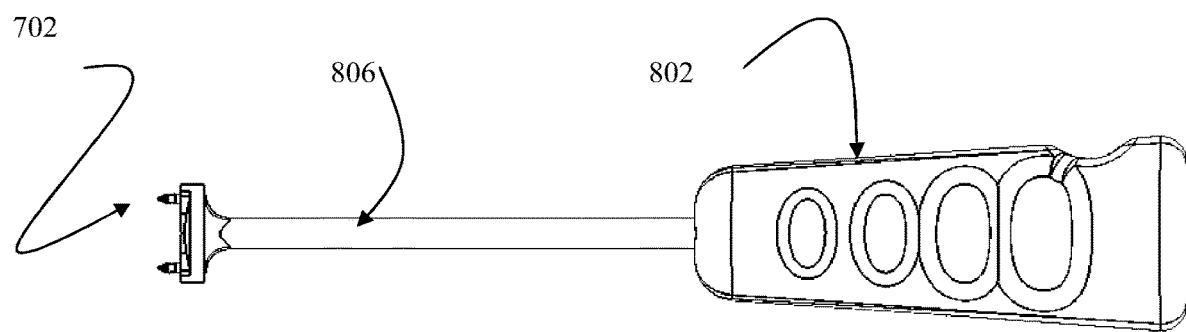
FIGS. 7A-E illustrate an embodiment of a posterior cervical facet staple gun in side view (FIG. 7A), oblique (FIG. 7B), exploded (FIG. 7C), cross-sectional (FIG. 7D), and front-on (FIG. 7E) views.
Figure 7B:
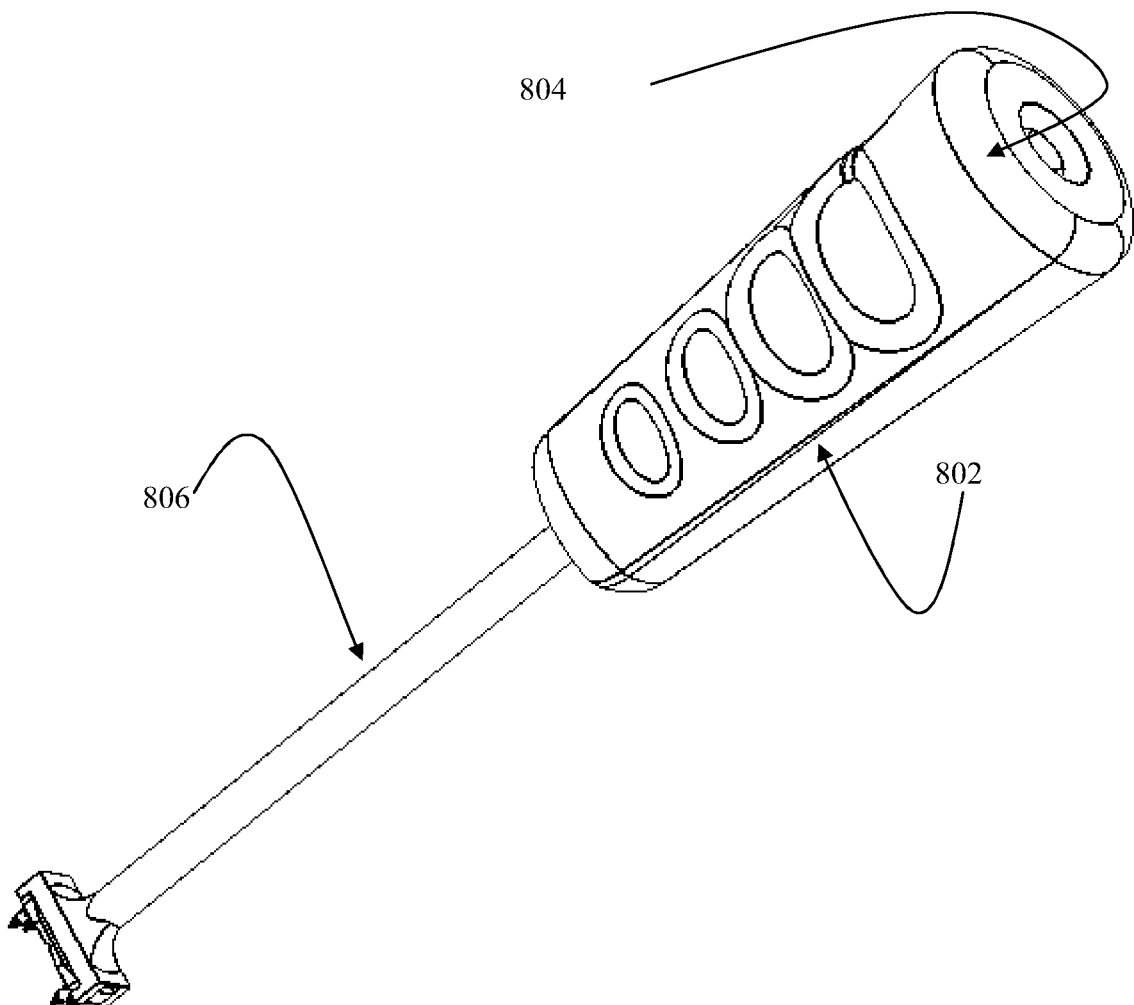
Figure 7C:
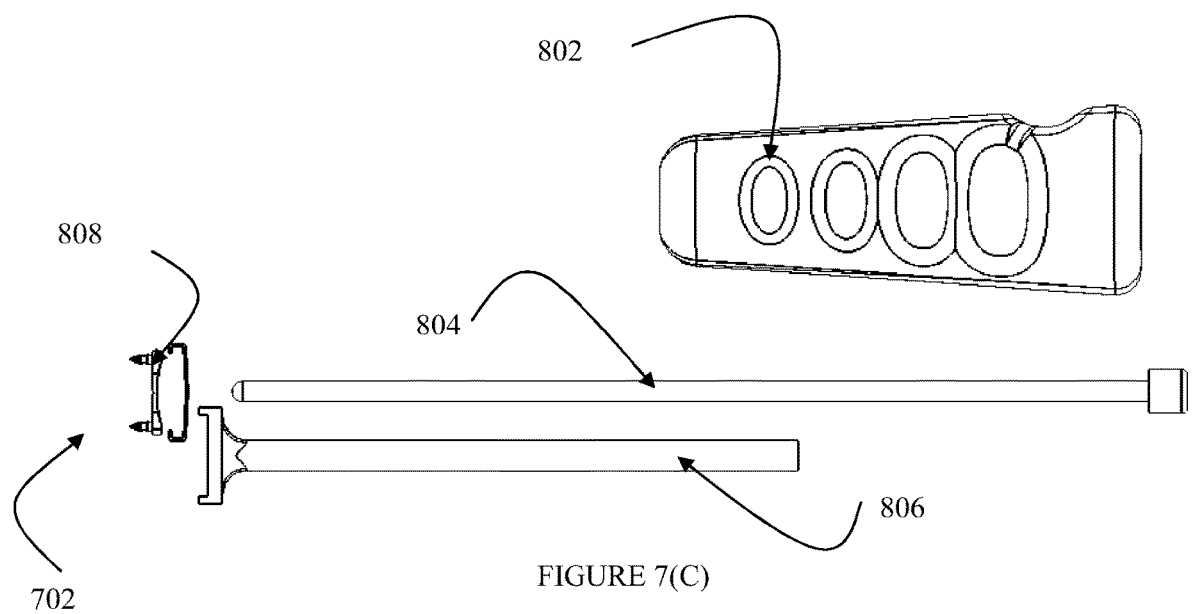
Figure 7D:
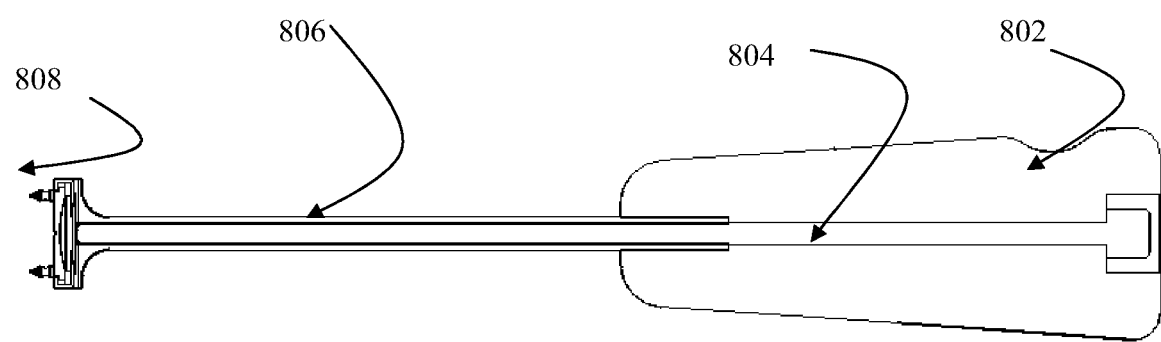
Figure 7E:
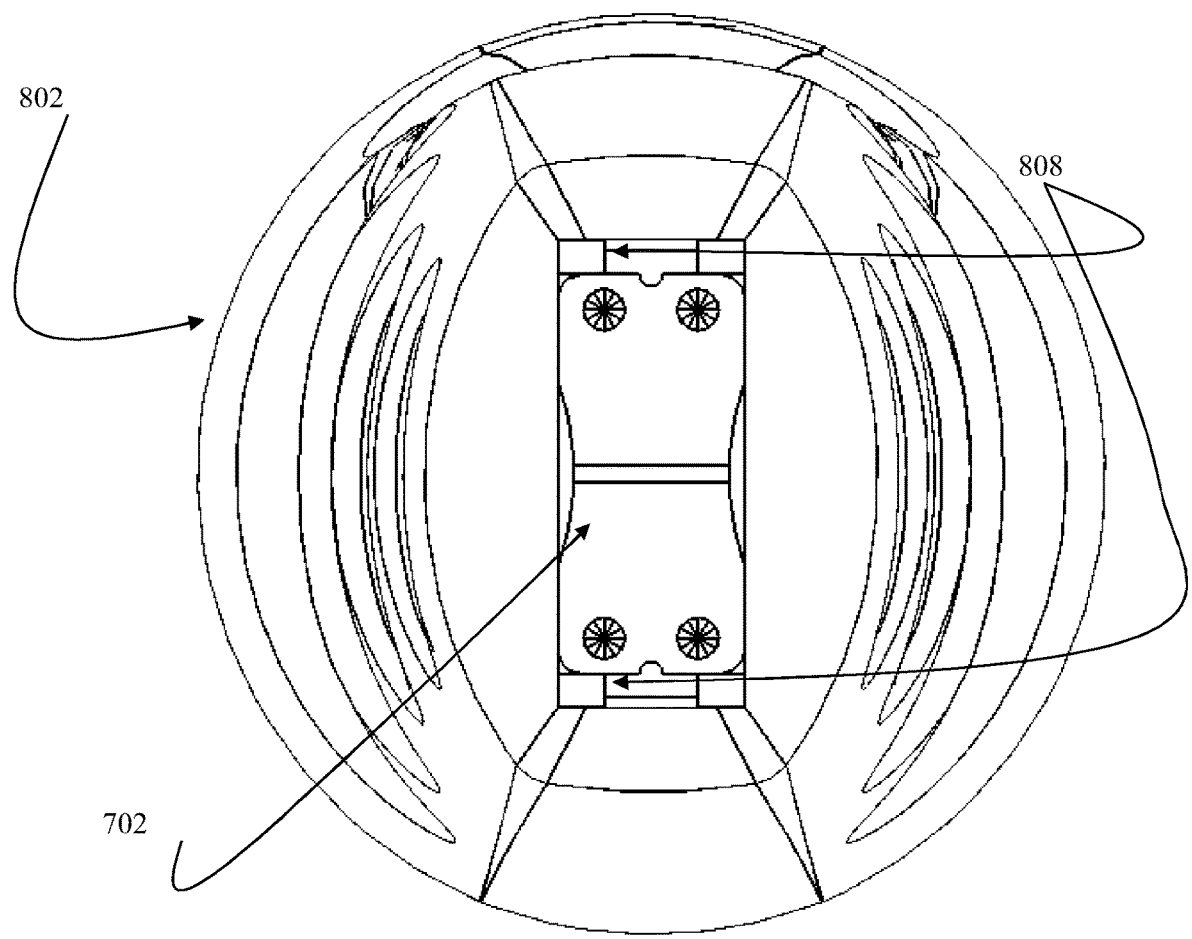
Figure 8A:
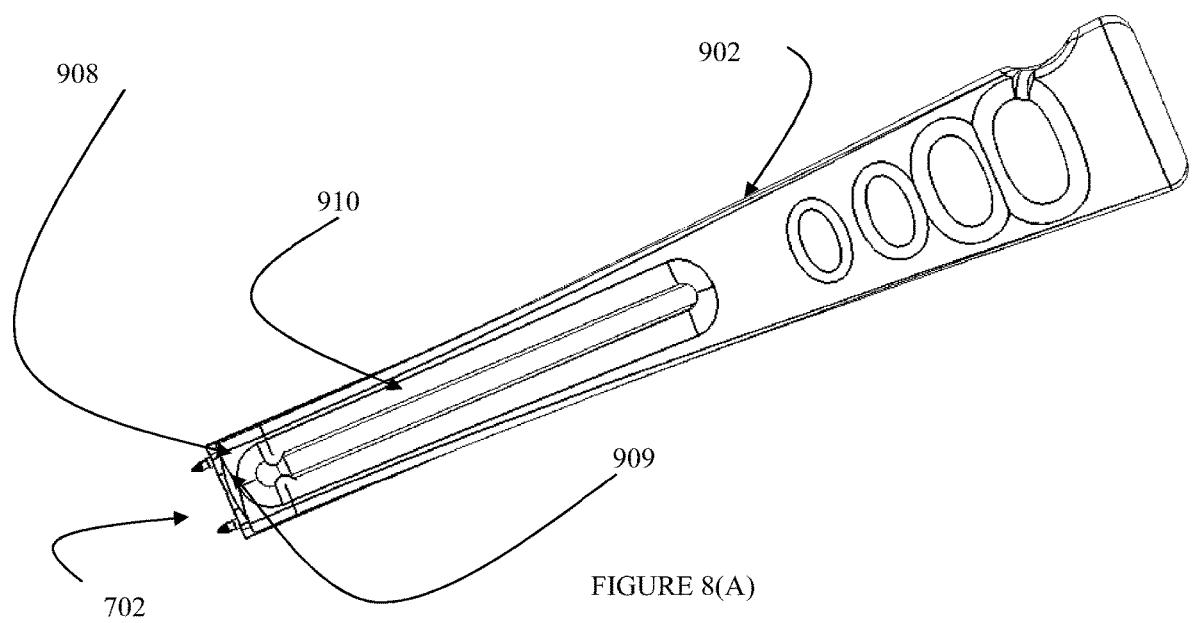
FIGS. 8A-E illustrate another embodiment of a posterior cervical facet staple gun in side view (FIG. 8A), oblique (FIG. 8B), exploded (FIG. 8C), cross-sectional (FIG. 8D), and front-on (FIG. 8E) views.
Figure 8B:
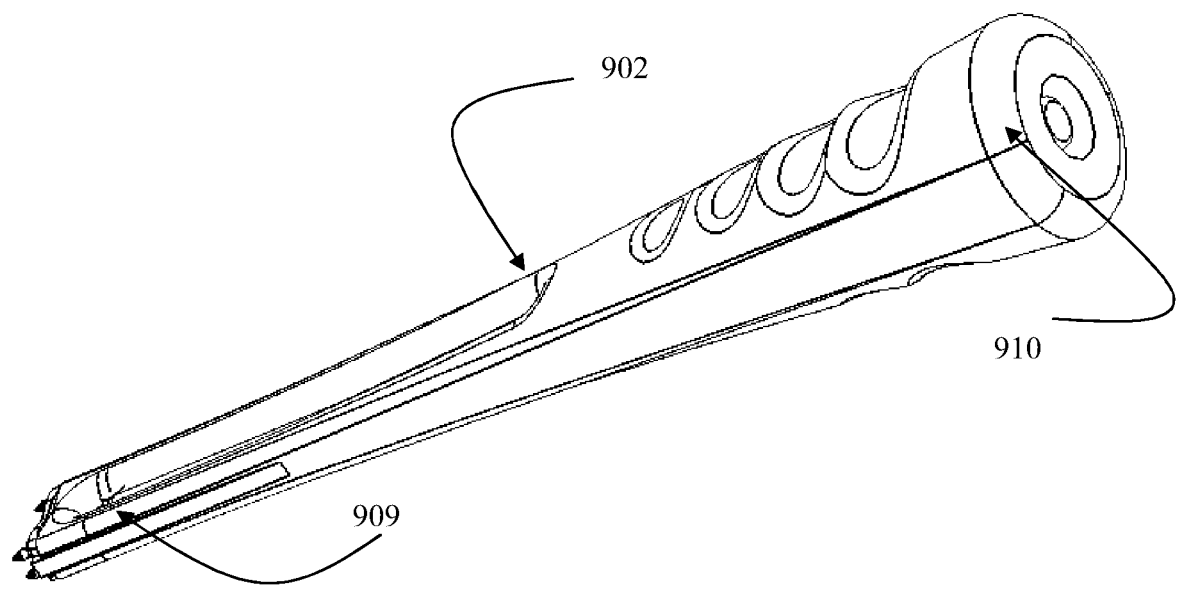
Figure 8C:
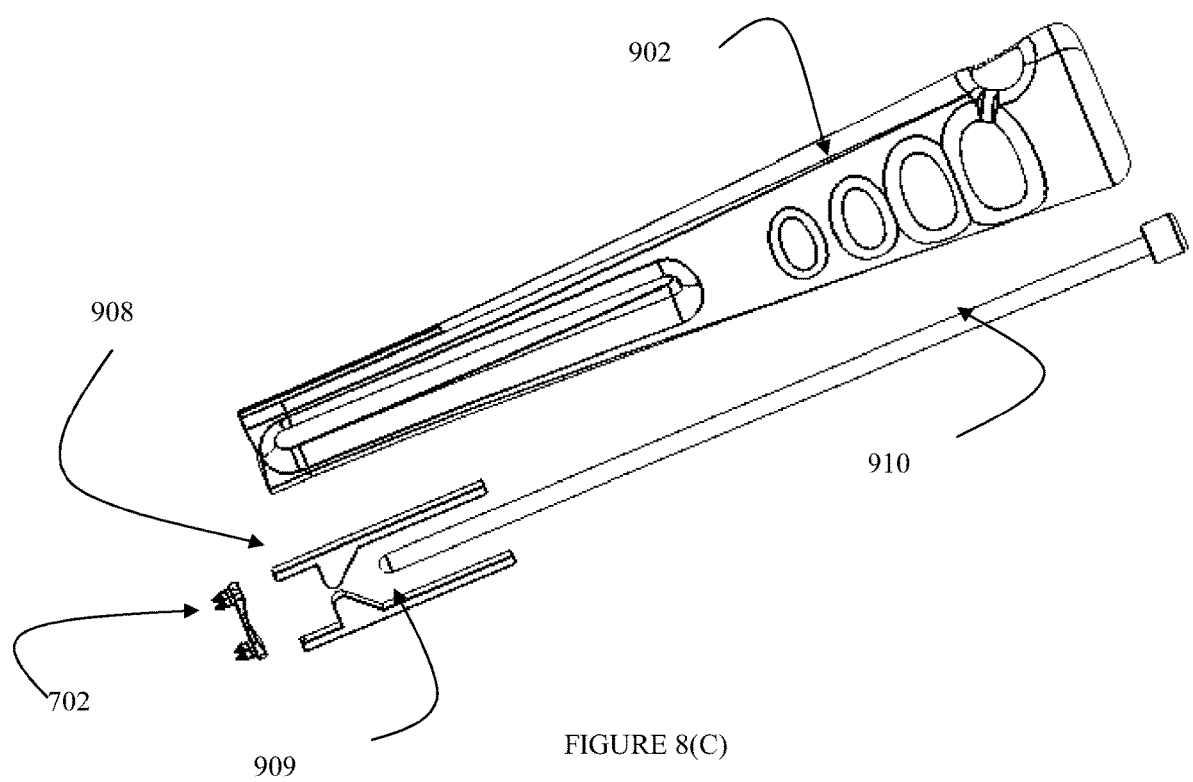
Figure 8D:
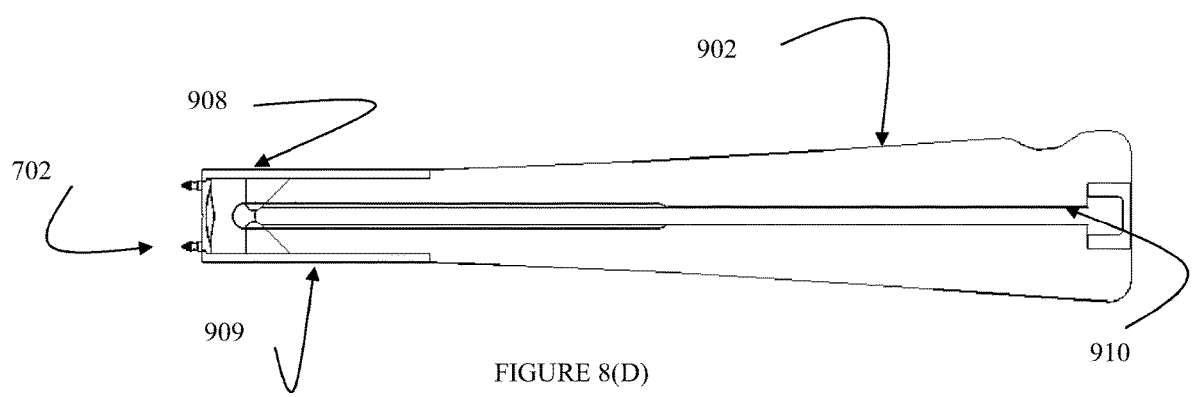
Figure 8E:
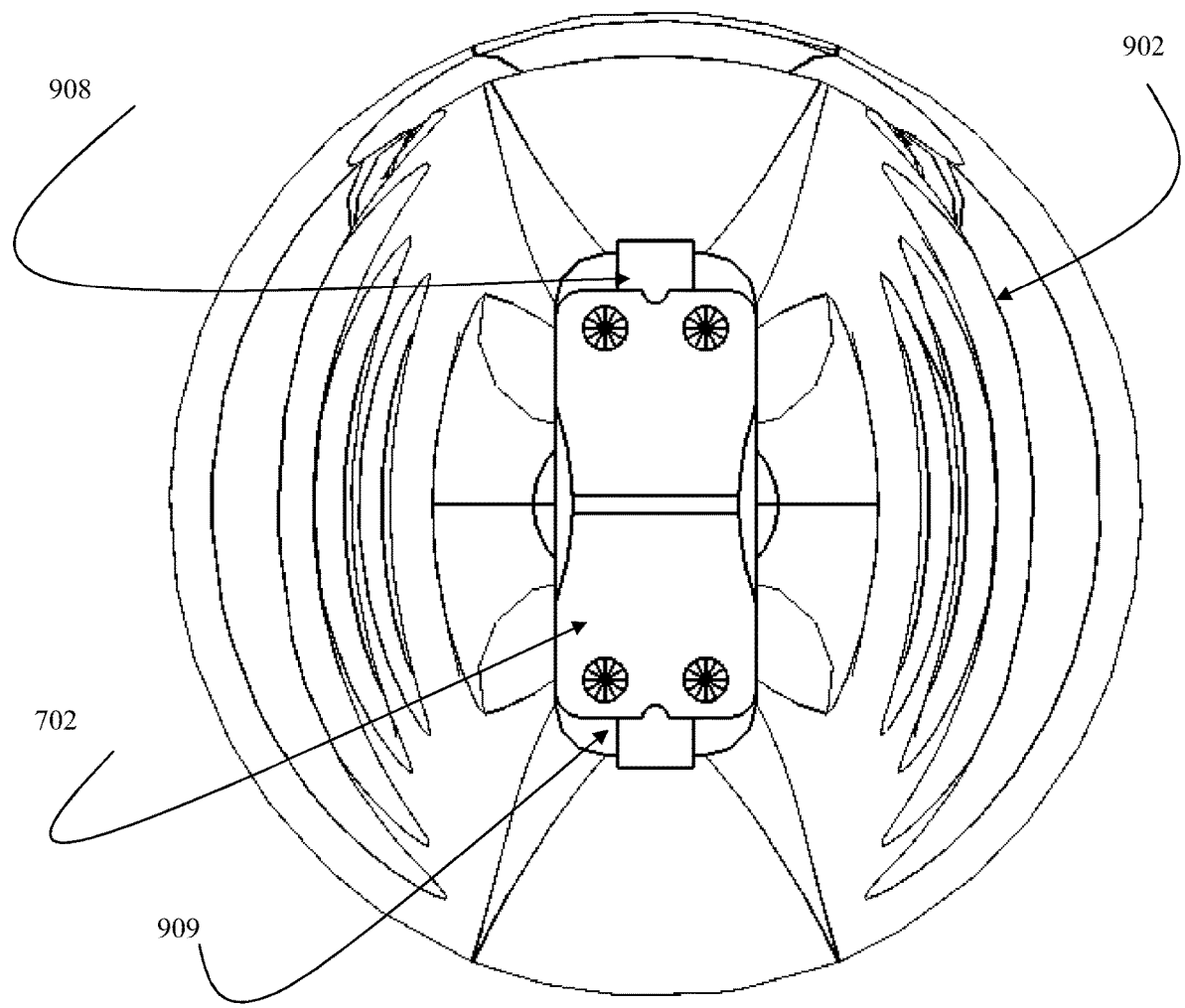

As illustrated in FIG. 5, a pliers device 40 for inserting and removing the locking mechanism can include a first arm rotatably coupled to a second arm; wherein each of the first arm and the second arm includes a handle portion on a first end; wherein the first arm includes an upper plier tip 42 and the second arm includes a lower plier tip 44, and wherein the first arm and the second arm engage the central screw locking lever 30. The upper plier tip 42 and the lower plier tip 44 each include a stop 46 configured to engage the bracket flexion grips 32. The pliers 40 can include a leaf spring 48 between the first arm and the second arm, wherein the leaf spring 48 biases the first handle portion away from the second handle portion. The pliers 40 can include a limiter 50 and limiting screw 52.

In an aspect of the pliers device 40 for inserting and removing a bi-directional fixating transvertebral (BDFT) screw/cage apparatus, the pliers device comprises a first arm rotatably coupled to a second arm; wherein each of the first arm and the second arm includes a handle portion on a first end; wherein the first arm includes an upper plier tip 42 and the second arm includes a lower plier tip 44, wherein the first arm and the second arm engage the bracket flexion grips 32, wherein the upper plier tip 42 and the lower plier tip 44 each include a stop 46 configured to engage the bracket flexion grips 32, and a leaf spring 48 between the first arm and the second arm, wherein the leaf spring 48 biases the first hand portion away from the second handle portion.

Another identical locking mechanism embodiment which includes a central rotating locking lever mechanism as designed for the cervical, thoracic and lumbosacral cage/BDFT constructs can likewise be designed for the posterior lumbosacral cage/BDFT constructs.

The exemplary embodiments of these locking mechanisms are another evolutionary embodiment not illustrated in the aforementioned related applications. The novel locking mechanisms are also is quite unique and different from other conventional locking mechanisms used for other known cervical and lumbar anterior or posterior plate screws. No other conventional posterior lumbar intervertebral cage BDFT/screw constructs are known.

FIGS. 6A-6D illustrate an embodiment of a lumbar facet joint staple gun.

Features of lumbar facet joint staple guns have been thoroughly described in the aforementioned related applications, the relevant portions of which are hereby incorporated by reference in their entirety. The exemplary staple gun 400 is an evolutionary advanced version compared to the conventional designs. The changes incorporated herein facilitate easier insertion and removal of the staple 700 compared to our prior design. An improved feature of the staple gun is the design of an independent puller tip which can be swung open when the stapler is at its maximum open position.

The figures illustrate the staple gun 400 which includes two upper and lower grips 404, 406, upper and lower bars 408, 410, a cylinder 418, a puller 414, a puller tip 402, a connector 418, a return spring 420, and pins 422.

In our previous design the user might have to force the staple hinge to fit into the loops (puller), and once the staple 700 was closed the user had to pry the staple hinge from the loops. To address this problem, one of the loops was made as an independent part which can be swung open when the stapler is at its maximum open position.

The following is the mechanism of its action: The user opens the stapler handles to their maximum. This forces the puller part 414 to stick out from the cylinder part 412. In that configuration, the puller tip 402 can be opened, and the user can insert the staple 700, and close the puller tip 402 (no force required). As the user closes the staple handles, the puller part 414 retracts into the cylinder part 412 which prevents the puller tip part 402 from opening. Thus there is no risk of the staple 700 becoming loose or falling off during surgery. Once the staple 700 has been closed, and is locked, the user can open once more the staple handles to their max to force the puller part out, and in that configuration, the puller tip 402 can be opened, and the staple 700 can be released. The release mechanism doesn't have a spring. The puller tip 402 can simply be opened only when the center shaft (puller) is extended completely. When the puller 414 is retracted (during stapling) the release (puller tip) is constrained by the surrounding geometry i.e. it cannot move. The main advantage of this mechanism is its simplicity. The spring 420 is for the return. The spring 420 pushes the puller out, so after the user staples, by pressing the handles together and pulling the center shaft in (puller), the spring 420 will force the puller 414 out and swing the handles open to reset the stapler.

For example, an aspect of the invention can include a staple gun for a lumbar facet joint staple includes a handle having an upper bar 408 and a lower bar 410, each of the upper bar 408 and the lower bar 410 having a first and a free end, a hollow cylinder 412 body having a first end for receiving the lumbar facet joint staple and a second end adjacent to the handle, a connector 418 having a first end coupled to the hollow cylinder 412 body and a second end coupled to the handle such that the first end of each of the upper bar 408 and the lower bar 410 can be pivotably coupled to the connector 418, a puller 414 disposed in and extending through the hollow cylinder 412 body, wherein the puller 414 has a first end for receiving the lumbar facet joint staple and a second end adjacent to the handle, the second end of the puller 414 being coupled to the handle, and a puller tip 402 coupled to the first end of the puller 414, wherein the handle can be moveable from a closed position to an open position, a distance between the free end of the upper bar 408 and the free end of the lower bar 410 in the closed position being less than a distance between the free end of the upper bar 408 and the free end of the lower bar 410 in the open position, wherein the first end of the puller 414 and at least a part of the puller tip 402 are disposed inside the first end of the hollow cylinder 412 body when the handle is in the closed position, and wherein the first end of the puller 414 and at least a part of the puller tip 402 extend outside the first end of the hollow cylinder 412 body when the handle is in the open.

The puller tip 402 can be moveable between an open position and a closed position when the handle in the open position, and wherein the puller tip 402 is locked in the closed position by the first end of the hollow cylinder 412 body when the handle in the closed position. The puller tip 402 can include a first loop part and a second loop part, the first loop part and the second loop part for grasping sides of the lumbar facet joint staple, wherein the first loop part is movable with respect to the second loop part in a direction transverse to a longitudinal axis of the puller 414. The staple gun can include a spring return mechanism that biases the handle in the open position. The handle can include a linkage coupling the puller 414 to each of the upper bar 408 and the lower bar 410.

Features of cervical facet joint staples have been thoroughly described in the aforementioned related applications, the relevant portions of which are hereby incorporated by reference in their entirety.

As shown in FIGS. 7A through 8E, an exemplary posterior cervical facet joint staple 702 includes a staple body extending along a longitudinal axis. The body includes a plurality of prongs extending from a lower surface of the staple body. The lower surface of the staple body also includes a groove for engaging or fitting into the spring supports of a staple gun (e.g., a cervical staple gun, as described in more detail below). The groove extends along an axis that is perpendicular to the longitudinal axis of the staple body. The groove is disposed at a center point along the longitudinal axis.

FIGS. 7 and 8 illustrate a four-prong embodiment. The cervical staple gun embodiments can also be used for a two pronged staple embodiment.

More particularly, the lumbar staple has top and bottom claws which come together. The top part of the staple, beneath from where the staple prongs come out, has on either side, a circular protuberance with a hole in the center. A pin goes through this hole and through a hole in the lower staple claw thus connecting these two components which pivot around the pin to open and close the jaw of the staple. The protuberances on both sides of the staple can be fit snugly into the puller tip 402 of the staple gun.

Exemplary aspects of a staple are illustrated in FIGS. 9A-B and 10A-C.

Figure 9A:
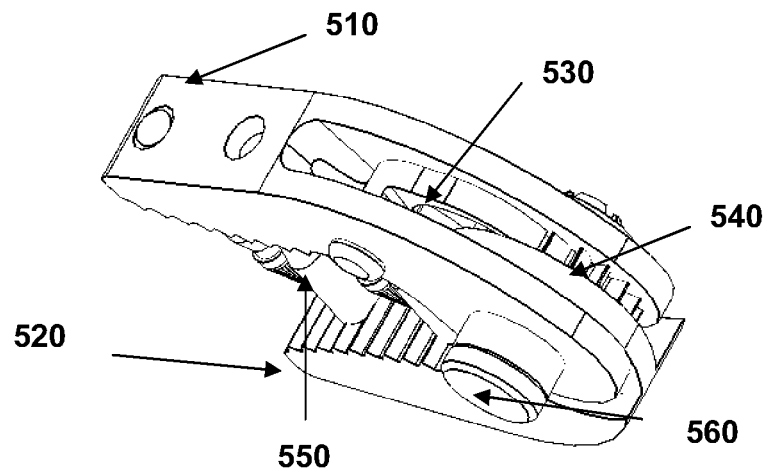
FIGS. 9A-B illustrate an embodiment of a posterior lumbar facet staple, flexure spring embodiment in side isometric (FIG. 9A) and exploded (FIG. 9B) views.
Figure 9B:
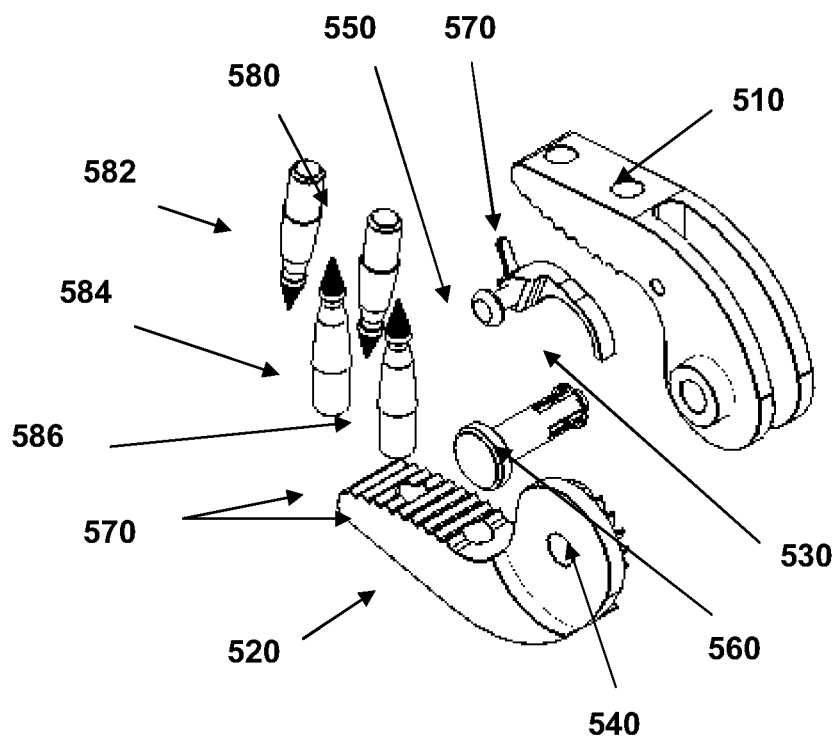
Figure 10A:
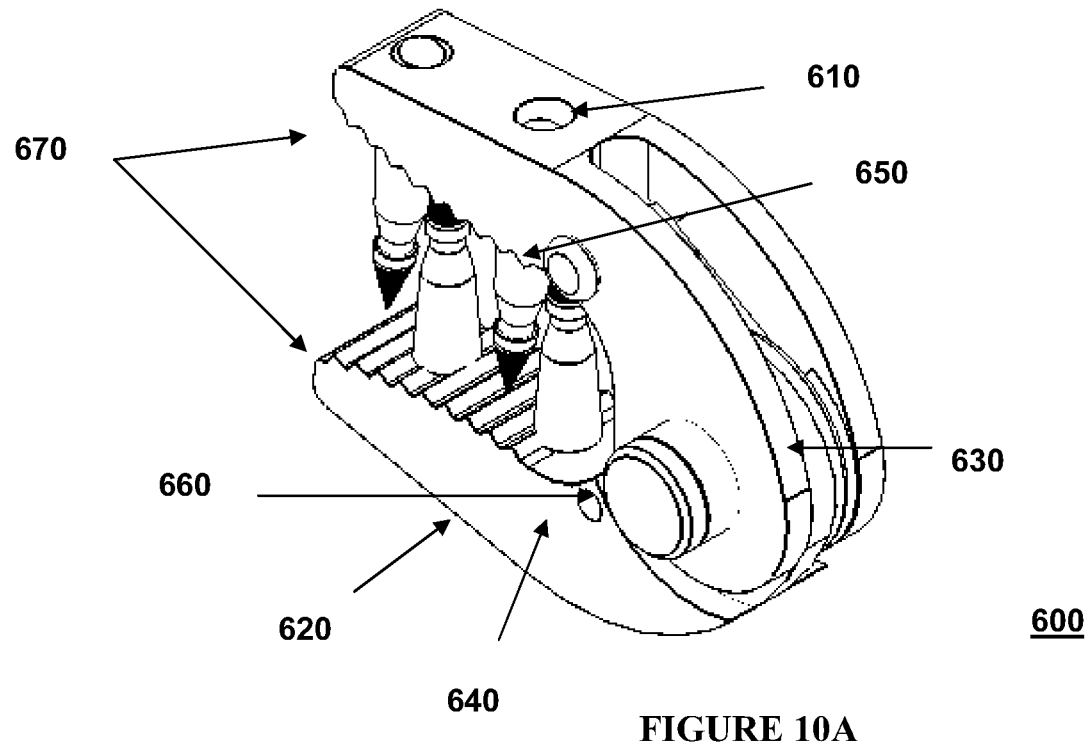
FIGS. 10A-C illustrate an embodiment of a posterior lumbar facet staple, torsional spring embodiment in side isometric (FIG. 10A), bottom isometric (FIG. 10B), and exploded (FIG. 10C) views.
Figure 10B:
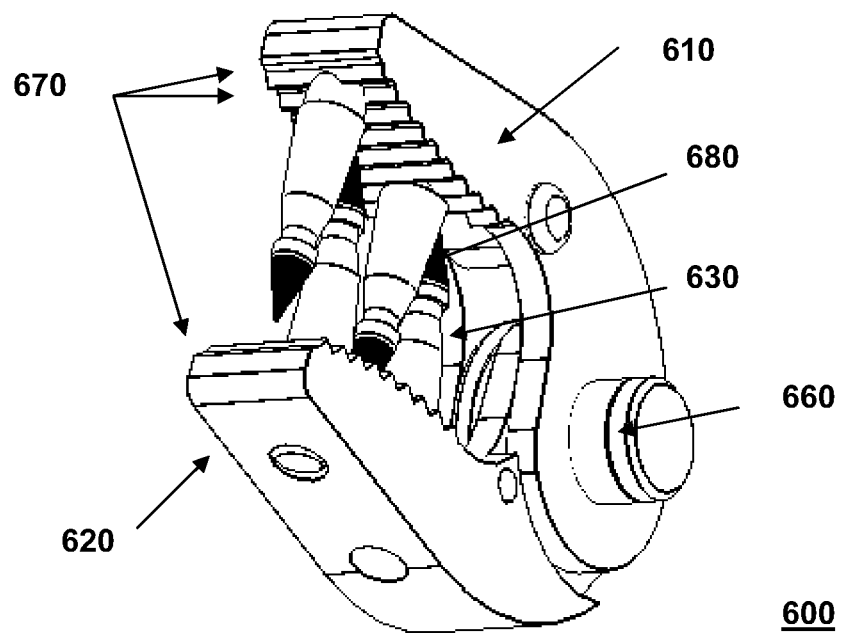
Figure 10C:
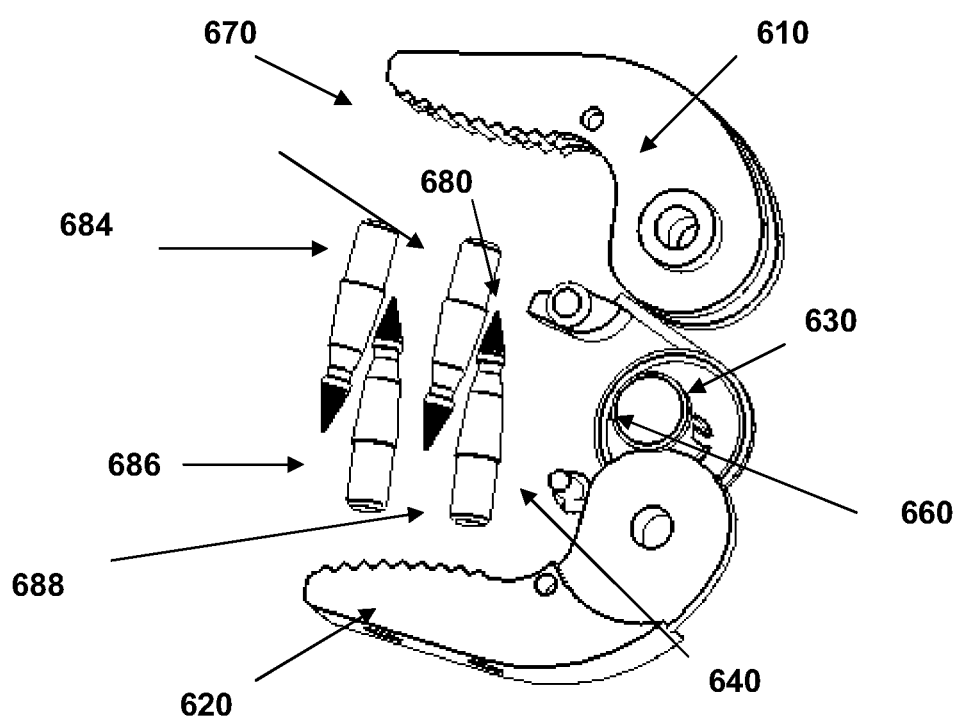

FIGS. 9A-B illustrate an embodiment of a posterior lumbar facet staple having a flexure spring. FIGS. 10A-C illustrate an embodiment of a lumbar facet staple having a torsional spring. Features of a lumbar facet staple have been thoroughly described in the aforementioned related applications, the relevant portions of which are hereby incorporated by reference herein in their entirety. The embodiments illustrated in the related applications included a ratchet. The staple could be incrementally closed with increased ratcheting over increasing number of spurs. The present invention provides two evolved embodiments, which are superior to conventional designs in that the closing mechanisms can withstand much greater force (Newtons) than a small external ratchet. Other improvements will be described below.

FIGS. 9A-B illustrate an embodiment of a posterior lumbar facet staple 500 having a flexure spring 530. As shown in FIGS. 9A-B, the features of the staple 500 include top claws 510 and bottom claws 520 with ridges 570 to help incorporate and fuse with bone. A staple pin (pivot) 560 connects the top claws 510 and bottom claws 520. The staple 500 includes four fastener pins (prongs) 580, 582, 584, 586, two per top claw 510 or bottom claw 520. Ratchet teeth 540 are molded onto the lower claw 520, and a spring loaded ratchet pawl 530 pivots on the claw, and locks the staple 500 in position. As the staple 500 closes, the ratchet 540 works in standard fashion. When a force is applied to open the staple 500, the ratchet 540 locks up, but the ratchet pawl (e.g., the flexure spring) 530 acts as a spring due to its curvature. So depending on the material used for the ratchet spring, the ratchet spring 530 can deform more or less, thereby providing different degrees of resistance. The ratchet mechanism 540 limits the opening force of the staple 500 by a force proportional to the stiffness of the flexure spring 530 (e.g., ratchet pawl). The force can be tailored by making the pawl from different materials or varying the dimension of the flexure spring on the pawl. This embodiment can achieve significant rigidity (stiffness).

FIGS. 10A-C illustrate an embodiment of a posterior lumbar facet staple 600 having a torsional spring 630. FIGS. 10A-C illustrate features of the staple 600, which include top claws 610 and bottom claws 620 with ridges 670 to help incorporate and fuse with bone. A staple pin (pivot) 660 joins the upper claw 610 and lower claw 620 of the staple 600. The staple 600 includes four fastener pins (prongs) 682, 684, 686, 688, two per top claw 610 or bottom claw 620 of the staple 600. The features of the staple 600 include a torsional spring 630, a brake 680, and a pivot spring pin 640. As the staple 600 closes, the ratchet works in standard fashion. When the staple 600 is open, the spring does not interfere with the motion. Once the staple 600 is closed there is a ratchet mechanism (brake) 680 that engages with the spring 630. At that point, the force required to open the staple 600 will depend on the stiffness of the spring 630.

Having staple models with different types of springs (e.g., soft, hard, etc.) allows the tailoring of different staples to the needs of a given patient. The embodiments of the present invention have less compliance than the conventional devices.

The staple gun embodiments illustrated in FIGS. 7 and 8 provide improved features over those previously described in our prior applications. The advantages of both these embodiments are their economic efficiency of design, their simplicity and their amenability to percutaneous surgical approaches.

FIGS. 7A-E illustrate an embodiment of a posterior cervical facet staple gun.

The internal mechanism includes a handle 802, a central staple plunger 804, a tip 806, and a retaining spring 808. A staple 702 is held in place at the tip 806 of the staple guide by a retaining spring 808. The device can be used with a hammer to apply a staple 702 (either two or four pronged). The spring 808 holding the staples 702 in place is a bi-staple spring that is opened to release a staple by pressing the center button (central plunger) of the handle 802. Pressing the central button opens up the spring 808, and the staple gun can then be reloaded with another staple 702.

FIGS. 8A-E illustrate another embodiment of a posterior cervical facet staple gun. The internal mechanism includes a handle 902, a plunger 910, and two mirror retaining springs 908, 909. The staple 702 is held in place at the tip of the staple guide by the retaining springs 908, 909. The device can be used with a hammer to impact the staple (either two or four pronged). A center button can be pressed to release the staple when needed. The staple gun can then be reloaded with another staple.

2. Surgical Method

Exemplary surgical steps for practicing one or more of the forgoing embodiments will now be described.

Anterior cervical spine placement of the intervertebral cage/BDFT screw construct (FIGS. 1-2) can be implanted via previously described techniques for anterior cervical discectomy and fusion. Some but not all of these techniques include, open, microscopic, closed endoscopic or tubular. Fluoroscopic or any other form of visualized guidance can be used for this procedure.

After the adequate induction of anesthesia the patient is placed in a supine position. An incision is made overlying the intended disc space or spaces, and the anterior spine is exposed. A discectomy is performed and the endplates exposed. The disc height is measured and an anterior cervical intervertebral cage of the appropriate disc height, width and depth is selected. The central cavity is packed with bone fusion material, autologous bone graft, allograft, alone or in combination with any commercially available bone fusion promoting product. The cage is then inserted into the midline of the anterior disc space routinely until it is flush or countersunk relative to the vertebral body above and below. The BDFT screws are then inserted into the internalized rostrally (superiorly) and caudally (inferiorly) angled screw guides. A drill with or without a drill guide can be used to prepare for screw placement. This is not absolutely necessary. Because the cage has internalized screw guides, self-drilling/self-tapping screws of the appropriately selected lengths can be directly screwed into the vertebral bodies once placed into the internalized drill-guided angled tunnels. The cage's screw guides, which have internalized tunnels, direct the screws into the superior and inferior vertebral bodies in the predetermined angle of the internalized tunnels. There is no other angled trajectory other than that which is built into the internalized screw guide/tunnel of the cage that the screw can be oriented in. Hence, there is no absolute need for fluoroscopic guidance.

Once the surgeon is satisfied with the position and placement of the cage, the BDFT screws can then be locked into their final positions. In the embodiment in FIG. 1, the patient rotates the central locking screw lever from the midline vertical position, ninety degrees; so that the locking lever handles lock the screws into position preventing screw pull-out. If the surgeon changes his mind intra-operatively or if in a future date the construct needs to be removed, the screw locking lever is rotated another ninety degrees, unblocking access to the screws, and the screws can be backed out. The locking mechanism has several cycles of use, and thus screws once backed out, can be re-screwed and re-locked. Multiple level placements can be performed including two, three or more levels if necessary.

For the embodiment illustrated in FIG. 2, once the surgeon is satisfied with the position and placement of the cage, the BDFT screws can then be locked in their final positions. Then a screw locking bracket is gently placed on top of the cage with the pliers (FIG. 5) allowing the bracket hooks to snap into the cage inserts. The plier tips have stops so that the brackets could be more easily held. It has a limiting screw that limits the amount the pliers close to prevent over-pressing the locking brackets. It also has a leaf spring that serves to pre-load the pliers. If the surgeon changes his mind intra-operatively, or if in a future date the construct needs to be removed, the surgeon presses on the side tabs with the pliers (FIG. 5) to slightly deform (open) the bracket hooks and easily remove it. The locking mechanism has several cycles of use, and thus screws once backed out, can be re-screwed and re-locked. Multiple level placements can be performed including two, three or more levels if necessary.

Anterior or anteriolateral placement of thoracic or lumbar spine intervertebral cage/BDFT screw constructs (FIG. 3) can be implanted via previously described surgical techniques for anterior lumbar discectomy, and transthoracic, anterior-lateral thoracic discectomy. Some but not all of these techniques include, open, microscopic, closed endoscopic or tubular. Fluoroscopic or any other form of visualized guidance can be used for this procedure.

After the adequate induction of anesthesia and after the anterior spine is exposed a discectomy is performed and the endplates exposed. The disc height is measured and an anterior lumbar (or thoracic) intervertebral cage of the appropriate disc height, width and depth is selected. The central cavity is packed with bone fusion material, autologous bone graft, allograft, alone or in combination with any commercially available bone fusion promoting product. The cage is then inserted into the midline of the anterior disc space routinely until it is flush or countersunk relative to the vertebral body above and below. The four BDFT screws are then inserted into the two middle internalized rostrally (superiorly) and two lateral, caudally (inferiorly) angled screw guides. A drill with or without a drill guide can be used to prepare for screw placement. This is not absolutely necessary. Because the cage has internalized screw guides, self-drilling/self-tapping screws of the appropriately selected lengths can be directly screwed into the vertebral bodies once placed into the internalized drill-guided angled tunnels. The cage's internalized guides, which have internalized tunnels, direct the screws into the superior and inferior vertebral bodies in the predetermined angle of the internalized tunnels. There is no other angled trajectory other than that which is built into the internalized screw guide/tunnel of the cage that the screw can be oriented in. Hence there is no absolute need for fluoroscopic guidance.

Once the surgeon is satisfied with the position and placement of the cage, the BDFT screws can then be locked in their final positions. Then a screw locking bracket is gently placed on top of the cage with the pliers (FIG. 5) allowing the bracket hooks to snap into the cage inserts. If the surgeon changes his mind intra-operatively, or if in a future date the construct needs to be removed, the surgeon presses on the side tabs with pliers (FIG. 5) to slightly deform (open) the bracket hooks and can then easily remove the locking bracket. The locking bracket has several cycles of use, and thus screws once backed out, can be re-screwed and re-locked. Multiple level placements can be performed including two, three or more levels if necessary.

Implantation of the posterior lumbar intervertebral cage/BDFT screw constructs (FIG. 4) can be performed via previously described posterior lumbar interbody fusion (PLIF) or posterior transforaminal lumbar interbody fusion (TLIF) procedures. The procedures can be performed open, microscopic, closed tubular or endoscopic techniques. Fluoroscopic guidance can be used with any of these procedures.

After the adequate induction of anesthesia, the patient is placed in the prone position. A midline incision is made for a PLIF procedure, and one or two parallel paramedian incisions or a midline incision is made for the TLIF procedure. For the PLIF procedure, a unilateral or bilateral facet sparing hemi-laminotomy is created to introduce the posterior lumbar construct into the disc space after a discectomy is performed and the space adequately prepared.

For the TLIF procedure, after unilateral or bilateral dissection and drilling of the inferior articulating surface and the medial superior articulating facet the far lateral disc space is entered and a circumferential discectomy is performed. The disc space is prepared and the endplates exposed.

The disc height is measured and a posterior lumbar intervertebral cage/BDFT screw construct (FIG. 4) of the appropriate disc height, width and depth is selected. The central cavity is packed with bone fusion material, autologous bone graft, allograft, alone or in combination with any commercially available bone fusion promoting product. Then one construct is placed on either right or left sides, or one construct each is placed into left and right sides. The constructs are inserted such they are flush or countersunk relative to the superior and inferior vertebral bodies. In addition to the central cavities that are packed with bone product, the intervertebral space in between the constructs can also be packed with bone product for fusion.

The BDFT screws are then inserted into internalized rostrally (superiorly) and caudally (inferiorly) angled screw guides. A drill with or without a drill guide can be used to prepare for screw placement. This is not absolutely necessary. Because the cage has internalized screw guides, self-drilling/self-tapping screws of the appropriately selected lengths can be directly screwed into the vertebral bodies once placed into the internalized drill-guided angled tunnels. The cage's internalized guides, which have internalized tunnels, direct the screws into the superior and inferior vertebral bodies in the predetermined angle of the internalized tunnels. There is no other angled trajectory other than that which is built into the internalized screw guide/tunnel of the cage that the screw can be oriented in. Hence, unlike posterior placement of pedicle screws there is no absolute need for fluoroscopic or expensive and cumbersome, frameless stereotactic CT guidance.

Once the surgeon is satisfied with the position and placement of the cage, the BDFT screws can then be locked in their final positions. Then a screw locking bracket is gently placed on top of the cage with the pliers (FIG. 5) allowing the bracket hooks to snap into the cage inserts. If the surgeon changes his mind intra-operatively, or if in a future date the construct needs to be removed, the surgeon presses on the side tabs with pliers (FIG. 5) to slightly deform (open) the bracket hooks and can then easily remove the locking bracket. The locking bracket has several cycles of use, and thus screws once backed out, can be re-screwed and re-locked. Multiple level placements can be performed including two, three or more levels if necessary.

The surgical placement of the lumbar facet staples via a posterior facet lumbar staple gun (FIG. 6) is described in the aforementioned related applications. The surgical procedure for these staple embodiments with this staple gun embodiment is identical to that which has been previously described. The evolutionary advantages of these embodiments are explained above.

For posterior placement of the cervical facet staples using the cervical facet staple gun embodiments (FIGS. 7-8), after the adequate induction of anesthesia the patient is flipped prone and his head and neck secured. A single midline or two paramedian incisions are made for unilateral or bilateral or multilevel placement of cervical staples. Ultimately the facet joint is exposed. Alternatively and preferably this can be performed percutaneously under fluoroscopic guidance with IV sedation. The cervical staple, two or four pronged is loaded either into the two or four pronged staple gun, is placed on the two articulating cervical facets, and then stapled into the joint using the staple gun. To achieve modular calibrated fusion, different combinations and permutations of cervical facet staples can be inserted ranging from a single unilateral two pronged staple providing a high degree of flexibility to a total of four bilaterally placed four pronged cervical staples leading to the highest degree of rigidity per cervical posterior joint. Additional bone may or may not be placed in the vicinity to facilitate permanent and solid fusion. These simplified and economically efficient cervical staple guns make this procedure amenable to percutaneous, precise staple placement, as well as contoured staple-bone integration.

The present inventions may provide effective and safe techniques that overcome the problems associated with current transpedicular based cervical, thoracic and lumbar fusion technology, as well as anterior cervical, thoracic and lumbar plating technology, and for many degenerative stable and unstable spinal diseases. These inventions could replace much pedicle screw, and anterior plating based instrumentation in many but not all degenerative spine conditions.

The speed and simplicity of placement of posterior cervical and lumbar facet staples, placement of anterior and posterior lumbar intervertebral cage/BDFT screw constructs, and placement of anterior cervical cage/BDFT screw constructs far exceeds that of current pedicle screw and anterior spinal plating technology. Furthermore, these devices have markedly significantly decreased risk of misguided screw placement and hence decreased risk of neurovascular injury, and blood loss. In the cervical and lumbar spines, intervertebral cage/BDFT screw constructs and facet staples could be applied modularly in different combinations to achieve different degrees of rigidity (flexibility). Furthermore, the posterior cervical and lumbar staple technology is amenable to short same-day procedures performed under local/IV anesthesia with a rapid recovery time. The lumbar and cervical intervertebral cage/BDFT screw constructs all would have decreased recovery time, and more rapid return to work time compared to pedicle screw, and plating technology. These devices with great probability lead to similar if not equal fusion rates, with substantially less morbidity, and hence, overall, make them a major advance in the evolution of spinal instrumented technology leading to advances in the compassionate care of the spinal patient.

For example, an aspect of the invention is directed to a method of inserting a bi-directional fixating transvertebral (BDFT) screw/cage apparatus between a first vertebral body and a second vertebral body, the method including inserting an intervertebral cage into a midline of a disc space between the first vertebral body and the second vertebral body until the intervertebral cage is one of flush and countersunk relative to the first vertebral body and the second vertebral body, inserting a first screw member into a first internal screw guide of the selected intervertebral cage, inserting a second screw member into a second internal screw guide of the selected intervertebral cage, screwing the first screw member and the second screw member into the first vertebral body and the second vertebral body respectively, and locking the first screw member and the second screw member in the intervertebral cage using a central screw locking lever coupled to the intervertebral cage, wherein the central screw locking lever prevents the first screw member and the second screw from pulling-out of the first internal screw guide and the second internal screw guide.

The central screw locking lever is rotatably coupled to the intervertebral cage, and the locking the first screw member and the second screw member in the intervertebral cage includes unlocking the first screw member and the second screw member, wherein the unlocking includes rotating the central screw locking lever with respect to the intervertebral cage from the locked position in which the central screw locking lever covers and locks the first screw member and the second screw member in the intervertebral cage to the unlocked position in which the first screw member and the second screw member are exposed.

The central screw locking lever includes a screw locking horizontal bracket, and wherein the locking includes press fitting the screw locking horizontal bracket on a top of the intervertebral cage such that the screw locking horizontal bracket covers and locks the first screw member and the second screw member in the intervertebral cage. The method can further include unlocking the first screw member and the second screw member, wherein the intervertebral cage includes hook insertion slots, wherein the screw locking horizontal bracket includes a cover portion extending in a direction of a longitudinal axis of the intervertebral cage and substantially parallel to a top face of the intervertebral cage, the cover portion covering and locking the first screw member and the second screw member in the intervertebral cage, side tabs on each end of the cover portion, wherein the side tabs extend in a direction perpendicular to the cover portion along the sides of the intervertebral cage, and wherein the side tabs include bracket hooks extending from the side tabs and lockingly engaging the hook insertion slots of the intervertebral cage, and bracket flexion grips for deforming the screw locking horizontal bracket, wherein the unlocking includes applying pressure to the bracket flexion grips to deform the screw locking horizontal bracket such that the side tabs of the screw locking bracket move away from the intervertebral cage and release the bracket hooks of the screw locking horizontal bracket from the hook insertion slots of the intervertebral cage.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. A bi-directional fixating transvertebral (BDFT) screw/cage apparatus, comprising:

first and second screw members;

an intervertebral cage for maintaining disc height, wherein the intervertebral cage includes:

a top wall, a bottom wall, and two sidewalls defining an open space capable of receiving bone filling for the biological bone fusion, wherein the open space extends between the top wall and the bottom wall and extends between the two sidewalls;

a first internal screw guide and a second internal screw guide defined by and extending through the top wall, wherein the first internal screw guide and the second internal screw guide each have an internal bore with an entry opening and an exit opening, the entry opening of the internal bore formed at least partially in a top surface of the top wall and the exit opening formed at least partially in a bottom surface of the top wall and at least partially in a side surface of the top wall, wherein each of the first internal screw guide and the second internal screw guide are angled to orient the first screw member and the second screw member bi-directionally; and a first vertebral body facing surface defined by the intervertebral cage and positioned so as to face a first vertebral body when the intervertebral cage is positioned in a disc space, wherein the first vertebral body facing surface includes a first plurality of ridges extending parallel to the top wall and the bottom wall;

a second vertebral body facing surface defined by the intervertebral cage and positioned so as to face a second vertebral body when the intervertebral cage is positioned in the disc space, wherein the second vertebral body facing surface includes a second plurality of ridges extending parallel to the top wall and the bottom wall;

a central screw locking lever coupled to the intervertebral cage, wherein the central screw locking lever comprises a first end sized and positioned to at least partially block the first screw member and the first internals screw guide, wherein the central screw locking lever comprises a second end sized and positioned to at least partially block the second screw member and the second internal screw guide, wherein the central screw locking lever comprises a middle extension configured to extend into the top wall at a location between the first and second internal screw guides such that the middle extension is rotatable with respect to the top wall of the intervertebral cage, wherein each of the first and second ends of the central screw locking lever are rounded when viewed from a direction perpendicular to the top wall, and wherein the central screw locking lever is configured to prevent the first screw member and the second screw member from pulling-out of the first internal screw guide and the second internal screw guide.

2. The apparatus of claim 1, wherein the intervertebral cage is a cervical cage sized and configured to be positioned in a cervical disc space.

3. The apparatus of claim 1, wherein the central screw locking lever has a width from the first end to the second end that is less than a width of the top wall of the intervertebral cage.

4. The apparatus of claim 1, wherein the first end of the central screw locking lever only partially blocks a first head of the first screw member and the second of the central screw locking lever only partially blocks a second head of the second screw member when the first and second screw members are inserted in the intervertebral cage and the central screw locking lever is positioned to block the first and second screw members.

5. The apparatus of claim 1, wherein first and second screw heads of the first and second screw members are partially visible behind the central screw locking lever when viewed from the direction perpendicular to the top wall.

6. The apparatus of claim 1, wherein outer surfaces of the first and second sidewalls each have a substantially flat portion positioned between the top and bottom walls and each have a substantially curved portion proximate the bottom wall.

7. The apparatus of claim 1, wherein each of the first and second sidewalls define slots that are positioned proximate the top wall.

8. The apparatus of claim 1, wherein the middle extension of the central screw locking lever has a diameter that is less than a width and a height of the both the first and second ends of the central screw locking lever.

9. The apparatus of claim 1, wherein the first and second screw members extend partially into the open space of the intervertebral cage when the first and second screw members are positioned in the first and second internal screw guides.

10. The apparatus of claim 1, wherein the central screw locking lever is pivotable with respect to the top wall of the intervertebral cage.

11. A bi-directional fixating transvertebral (BDFT) screw/cage apparatus, comprising:
first and second screw members;
an intervertebral cage for maintaining disc height, wherein the intervertebral cage includes:
a top wall, a bottom wall, and two sidewalls defining an open space capable of receiving bone filling for the biological bone fusion, wherein the open space extends between the top wall and the bottom wall and extends between the two sidewalls;
a first internal screw guide and a second internal screw guide defined by and extending through the top wall, wherein the first internal screw guide and the second internal screw guide each have an internal bore with an entry opening and an exit opening, the entry opening of the internal bore formed entirely in a top surface of the top wall and the exit opening formed at least partially in a bottom surface of the top wall and at least partially in a side surface of the top wall, wherein each of the first internal screw guide and the second internal screw guide are angled to orient the first screw member and the second screw member bi-directionally; and
a first vertebral body facing surface defined by the intervertebral cage and positioned so as to face a first vertebral body when the intervertebral cage is positioned in a disc space, wherein the first vertebral body facing surface includes a first plurality of surface features configured to facilitation integration and fusion;
a second vertebral body facing surface defined by the intervertebral cage and positioned so as to face a second vertebral body when the intervertebral cage is positioned in the disc space, wherein the second vertebral body facing surface includes a second plurality of surface features configured to facilitation integration and fusion;
a central screw locking lever coupled to the intervertebral cage, wherein the central screw locking lever comprises a first end sized and positioned to at least partially block the first screw member and the first internals screw guide, wherein the central screw locking lever comprises a second end sized and positioned to at least partially block the second screw member and the second internal screw guide, wherein the central screw locking lever comprises an extension positioned at or near a central portion between the first and second ends and is configured to extend into the top wall at a location at least partially between the first and second internal screw guides such that the extension is rotatable with respect to the top wall of the intervertebral cage, wherein each of the first and second ends of the central screw locking lever are rounded when viewed from a direction perpendicular to the top wall, and wherein the central screw locking lever is configured to prevent the first screw member and the second screw member from pulling-out of the first internal screw guide and the second internal screw guide.

12. The apparatus of claim 11, wherein the intervertebral cage is a cervical cage sized and configured to be positioned in a cervical disc space.

13. The apparatus of claim 11, wherein the central screw locking lever has a width from the first end to the second end that is less than a width of the intervertebral cage from the first sidewall to the second sidewall.

14. The apparatus of claim 11, wherein the first end of the central screw locking lever only partially blocks a first head of the first screw member and the second of the central screw locking lever only partially blocks a second head of the second screw member when the first and second screw members are inserted in the intervertebral cage and the central screw locking lever is positioned to block the first and second screw members.

15. The apparatus of claim 11, wherein first and second screw heads of the first and second screw members are partially visible behind the central screw locking lever when viewed from the direction perpendicular to the top wall.

16. The apparatus of claim 11, and further comprising:
allograft bone fusion material placed in the open space of the intervertebral cage, wherein the bone product is configured to facilitate fusion.

17. The apparatus of claim 11, wherein each of the first and second sidewalls define slots that are positioned proximate the top wall.

18. The apparatus of claim 11, wherein the extension of the central screw locking lever has a diameter that is less than a width and a height of the both the first and second ends of the central screw locking lever.

19. The apparatus of claim 11, wherein the first and second screw members extend partially into the open space of the intervertebral cage when the first and second screw members are positioned in the first and second internal screw guides.

20. The apparatus of claim 11, wherein the central screw locking lever is pivotable with respect to the top wall of the intervertebral cage.

* * * * *